United States Patent
Cohen et al.

(10) Patent No.: US 12,398,110 B2
(45) Date of Patent: Aug. 26, 2025

(54) SECOND GENERATION INHIBITORS OF MITOCHONDRIAL PERMEABILITY TRANSITION PORE WITH IMPROVED PLASMA STABILITY

(71) Applicant: Oregon Health & Science University, Portland, OR (US)

(72) Inventors: Michael Cohen, Portland, OR (US); Michael Forte, Portland, OR (US); Justina Sileikyte, Portland, OR (US); Aaron Nilsen, Portland, OR (US); Jordan Devereaux, Portland, OR (US); Paolo Bernardi, Padua (IT)

(73) Assignee: Oregon Health & Science University, Portland, OR (US)

( * ) Notice: Subject to any disclaimer, the term of this patent is extended or adjusted under 35 U.S.C. 154(b) by 807 days.

(21) Appl. No.: 17/636,327

(22) PCT Filed: Jul. 24, 2020

(86) PCT No.: PCT/US2020/043609
§ 371 (c)(1),
(2) Date: Feb. 17, 2022

(87) PCT Pub. No.: WO2021/016594
PCT Pub. Date: Jan. 28, 2021

(65) Prior Publication Data
US 2022/0289690 A1 Sep. 15, 2022

Related U.S. Application Data

(60) Provisional application No. 62/878,278, filed on Jul. 24, 2019.

(51) Int. Cl.
*C07D 249/06* (2006.01)
(52) U.S. Cl.
CPC .................. *C07D 249/06* (2013.01)
(58) Field of Classification Search
CPC .................................................. C07D 249/06
See application file for complete search history.

(56) References Cited

U.S. PATENT DOCUMENTS 7,078,426 B2  7/2006  Hogenkamp et al.
2018/0282264 A1  10/2018  Roy

OTHER PUBLICATIONS

Antonucci, et al., "A novel class of cardioprotective small-molecule PT inhibitors," Pharmacological Research, vol. 151, 2020, 12 pages.
Bonandi, et al., "The 1,2,3-triazole ring as a bioisostere in medical chemistry," Drug Discovery Today, vol. 22, No. 10, 2017, pp. 1572-1581.
Budzik, et al., "Synthesis and structure-activity relationships of a series of 3-aryl-4-isoxazolecarboxamides as a new class of TGRS agonists," Bioorganic & Medicinal Chemistry Letters, vol. 20, 2010, pp. 1363-1367.
Filimonov, et al., "Unusually Stable, Versatile, and Pure Arenediazonium Tosylates: Their Preparation, Structures, and Synthetic Applicability," Organic Letters, vol. 10, No. 18, 2008, pp. 3961-3964.
Roy, et al., "Discovery, Synthesis, and Optimization of Diarylisoxazole-3-carboxamides as Potent Inhibitors of the Mitochondrial Permeability Transition Pore," ChemMedChem. vol. 10, No. 10, 2015, pp. 1655-1671.
Roy, et al., "N-Phenylbenzamides as Potent Inhibitors of the Mitochondrial Permeability Transition Pore," ChemMedChem, vol. 11, No. 3, 2016, pp. 283-288.

*Primary Examiner* — Shawquia Jackson
(74) *Attorney, Agent, or Firm* — Lee & Hayes, P.C.

(57) ABSTRACT

The present invention provides compounds useful as mitochondrial permeability transition pore (mtPTP) inhibitors, the compounds being of Formula (I), or a pharmaceutically acceptable salt thereof wherein $R_1$ is selected from the group of H, halogen, and $C_1$-$C_3$ alkyl; and $R_2$ is selected from the group of H, $CF_3$, and halogen; with the proviso that at least one of $R_1$ and $R_2$ is halogen or $CF_3$.

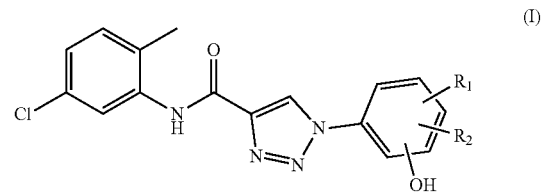

(I)

8 Claims, 13 Drawing Sheets
Specification includes a Sequence Listing.

SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: synthetic guide RNA for CRISPR system; shown as
      DNA

<400> SEQUENCE: 1
ccgacccgcg cccgcgatgc tgg                                                 23

<210> SEQ ID NO 2
<211> LENGTH: 25
<212> TYPE: DNA
<213> ORGANISM: artificial
<220> FEATURE:
<223> OTHER INFORMATION: Morpholino

<400> SEQUENCE: 2
gagagcggaa gacgaacctt cattc                                               25

<210> SEQ ID NO 3
<211> LENGTH: 25
<212> TYPE: DNA
<213> ORGANISM: Artificial Sequence
<220> FEATURE:
<223> OTHER INFORMATION: Morpholino Control

<400> SEQUENCE: 3
cctcctacct cagttacaat ttata                                               25

SECOND GENERATION INHIBITORS OF MITOCHONDRIAL PERMEABILITY TRANSITION PORE WITH IMPROVED PLASMA STABILITY

CROSS-REFERENCE TO RELATED APPLICATIONS

This application is the U.S. National Phase of PCT/US2020/043609, filed Jul. 24, 2020; which claims priority to and the benefit of the earlier filing of U.S. Provisional Application No. 62/878,278, filed on Jul. 24, 2019, which is incorporated by reference herein in its entirety.

REFERENCE TO SEQUENCE LISTING

The nucleic acid and/or amino acid sequences described herein are shown using standard letter abbreviations, as defined in 37 C.F.R. § 1.822. A computer readable text file, entitled "2N94453.txt (Sequence Listing.txt)" created on or about Feb. 16, 2022, with a file size of 4 KB, contains the sequence listing for this application and is hereby incorporated by reference in its entirety.

FIELD OF THE INVENTION

The present invention concerns compounds useful as mitochondrial permeability transition pore (mtPTP) inhibitors, as well as pharmaceutical compositions comprising them. In some embodiments are provided treatments of diseases and/or conditions associated with mtPTP function, such as those for multiple sclerosis, amyotrophic lateral sclerosis, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, diabetic retinopathy, muscular dystrophy, heart infarction, and stroke. The present invention is also generally applicable toward the treatment of disorders governed at least in part by an over-accumulation of reactive oxygen species and/or [$Ca^{2+}$] dysregulation.

BACKGROUND OF THE INVENTION

Mitochondrial permeability transition pore (mtPTP) channels play a significant role in a number of human diseases states where common pathology is based upon mitochondrial dysfunction. Mitochondrial permeability transition pore (mtPTP) is a high-conductance channel of the inner mitochondrial membrane (IMM) mediating $Ca^{2+}$ release and affected by voltage, pH and, cyclosporin A (CsA), and activated by an accumulation of mitochondrial $Ca^{2+}$ and oxidative stress.

Published U.S. Patent Application No. 2018/0282264 (Roy et al.) teaches small molecule mtPTP inhibitors, particularly including those having N,5-diphenylisoxazole-3-carboxamide, N,5-diphenyl-1H-pyrazole-3-carboxamide, 5-oxo-N,1-diphenylpyrrolidine-3-carboxamide, 5-oxo-1-phenyl-N-(pyridin-3-yl)pyrrolidine-3-carboxamide, and 4-phenyl-N-(pyridin-3-yl)furan-2-carboxamide scaffolds.

There remains a need for compounds, pharmaceutical compositions, and methods that effectively inhibit of the mtPTP. Compounds that prevent mtPTP opening are useful in treating and preventing cellular damage, [$Ca^{2+}$] dysregulation, and/or the reactive oxygen species associated with oxidative stress-related disorders.

SUMMARY OF THE INVENTION

Provided herein are compounds, pharmaceutical compositions, and methods of treatment comprising and utilizing compounds useful as inhibitors of the mitochondrial permeability transition pore (mtPTP).

In one embodiment is provided a compound of Formula (I), or a pharmaceutically acceptable salt thereof:

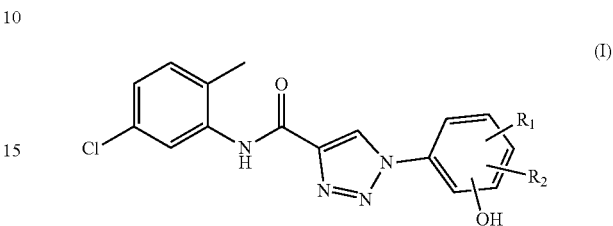

wherein $R_1$ is selected from the group of H, halogen, and $C_1$-$C_3$ alkyl;
and $R_2$ is selected from the group of H, $CF_3$, and halogen;
with the proviso that at least one of $R_1$ and $R_2$ is halogen or $CF_3$.

BRIEF DESCRIPTION OF THE SEVERAL VIEWS OF THE DRAWINGS

FIGS. 3I-3D graphs compound TR001 prevention of chemical activation induced mitochondrial swelling. FIG. 3A-3D) mouse liver mitochondria (0.25 mg/mL) were treated with 10 μM $Ca^{2+}$ only (traces a); 10 μm $Ca^{2+}$ and after 2 min of incubation with: FIG. 3A) 7 μm PhAsO, FIG. 3B) 2 mm Diamide, FIG. 3C), 7 μm Cu(OP)$_2$, FIG. 3D), 2 mm NEM (traces b-d). In traces c and d additions were as in traces b except that mitochondria were also treated with 1.5 μmCsA (traces c) or TR001 (traces d). Traces are representative of n=4 independent preparations.

FIG. 4A, CRC ratios of mouse liver mitochondria treated with TR001 only (trace a) or in combination with 2 μm CsA (trace b). Data are average±SEM of 7 and 5 independent preparations, respectively. FIG. 4B, CRCs of permeabilized HEK293T WT or CyPD KO cells treated with DMSO, 10 μm CsA or 10 μm TR001. Each spike in fluorescence indicates 10 μm $Ca^{2+}$ injection. Traces are representative of 4 independent preparations.

FIG. 5B, Respiratory control ratios of isolated mitochondria. FIG. 5D, Interference with HeLa cell proliferation after 24 h treatment with TR001. FIG. 5B and FIG. 5D, data are average±SEM of 4 and 6 independent experiments.

FIG. 6A represents spontaneous coiling events were recorded at 24 hours post-fertilization (hpf) in DMSO-treated zebrafish injected with the scrambled morpholino (scrd_MO), DMSO-treated col6a1 morphants (col6a1_MO) and col6a1 morphants (col6a1_MO) treated with the indicated concentrations of TR001 or 63. Data report the number of spontaneous coiling events in 15 seconds and are reported as mean±SEM of 6 independent experiments (n=52 for each condition); p<0.01, *p<0.001 as analyzed by one-way ANOVA with Bonferroni correction.

FIG. 6B graphs touch-evoked escape responses were recorded at 48 hpf. Embryos were divided in four subgroups according the phenotype observed: paralyzed (black bar), coiling only (gray bar), low motility (hatched bar) and normal (white bar). Data are reported as percentage of these phenotypes per each treatment condition. Comparison between groups were made using $\chi^2$ test and one-way ANOVA with Bonferroni correction; #/*p<0.05, ##/p<0.01, ###/*p<0.001. The symbol * is for statistical analysis comparing DMSO-treated col6a1 morphants (col6a1_MO) and those treated with increasing doses of both TR001 and 63; the symbol # is used for statistical analysis comparing the two groups of col6a1_MO treated with TR001 or 63. Six independent experiments were performed.

FIG. 6C graphs birefringence was measured at 48 hpf and zebrafish embryos were divided in 3 subgroups according the phenotype observed: normal (white bar), mild (gray bar) and severe (black bar) phenotype. Four independent experiments were performed and the final number of zebrafish embryo per group was 40 for each condition. Data are reported as the percentage of birefringence phenotypes. Data were analyzed by using $\chi^2$ test and one-way ANOVA with Bonferroni correction; #/*p<0.5, ##/p<0.01, ###/*p<0.001.

FIG. 6D depicts oxygen consumption rates (OCR) measured on entire zebrafish embryos at 48 hpf.

DETAILED DESCRIPTION OF THE INVENTION

Figure 1A:
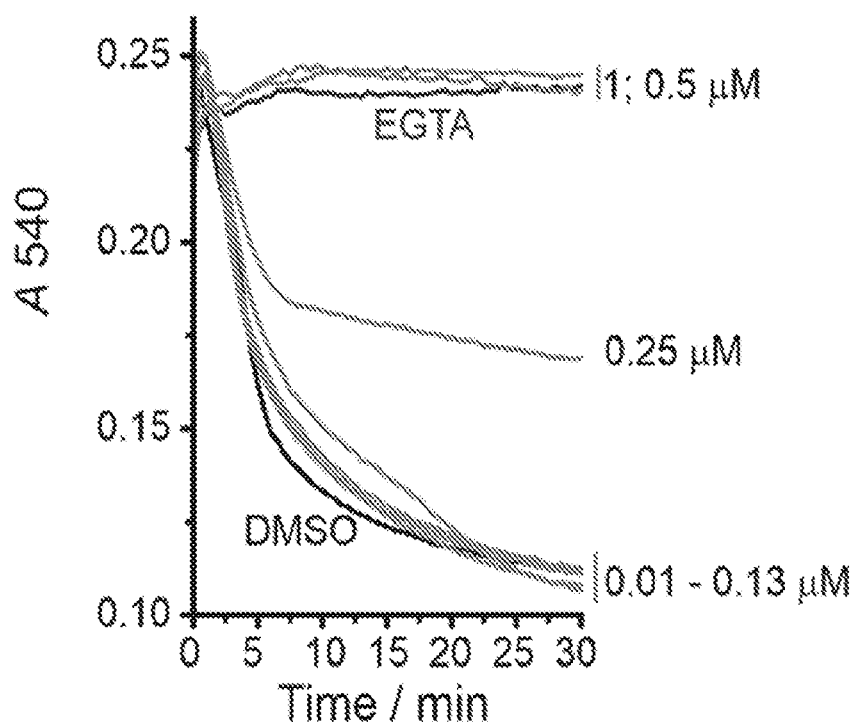
FIG. 1A represents effects of Cyclosporin A (CsA) on mtPTP. A) Representative traces of effect of indicated concentrations of CsA on $Ca^{2+}$ overload (60 μm) induced mitochondrial swelling in isolate mouse liver mitochondria.

Also provided is a compound of Formula (I), or a pharmaceutically acceptable salt thereof,

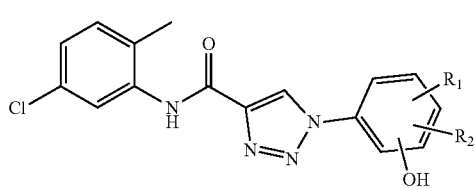

(I)

wherein $R_1$ is selected from the group of H, F, Cl, Br, and $C_1$-$C_3$ alkyl; and $R_2$ is selected from H, F, Cl, and Br; with the proviso that at least one of $R_1$ and $R_2$ is selected from the group of $CF_3$, F, Cl, and Br.

Also provided is a compound of Formula (I), or a pharmaceutically acceptable salt thereof, wherein $R_1$ is selected from the group of H, F, Cl, Br, and $C_1$-$C_3$ alkyl; and $R_2$ is selected from H, F, Cl, and Br; with the proviso that at least one of $R_1$ and $R_2$ is selected from the group of $CF_3$ and F.

Another embodiment provides compound of Formula (I), wherein $R_1$ is F; and $R_2$ is selected from the group of H, methyl, F, Br, and Cl; or a pharmaceutically acceptable salt thereof.

Another embodiment provides compound of Formula (I), wherein $R_1$ is Cl; and $R_2$ is selected from the group of H, methyl, F, Br, and Cl; or a pharmaceutically acceptable salt thereof.

Still another embodiment provides a compound of Formula (I), wherein $R_1$ is Br; and $R_2$ is selected from the group of H, methyl, F, Br, and Cl; or a pharmaceutically acceptable salt thereof.

Another embodiment provides compound of Formula (I), wherein $R_1$ is F; and $R_2$ is H; or a pharmaceutically acceptable salt thereof.

Another embodiment provides compound of Formula (I), wherein $R_1$ is H; and $R_2$ is $CF_3$; or a pharmaceutically acceptable salt thereof.

Another embodiment provides compound of Formula (I), wherein $R_1$ is methyl; and $R_2$ is H; or a pharmaceutically acceptable salt thereof.

Another embodiment provides compound of Formula (I), wherein $R_1$ is Cl; and $R_2$ is H; or a pharmaceutically acceptable salt thereof.

Still another embodiment provides a compound of Formula (I), wherein $R_1$ is Br; and $R_2$ is H; or a pharmaceutically acceptable salt thereof.

Another embodiment provides compound of Formula (I), wherein $R_1$ is F; and $R_2$ is F; or a pharmaceutically acceptable salt thereof.

Another embodiment provides a compound of Formula (II), or a pharmaceutically acceptable salt thereof:

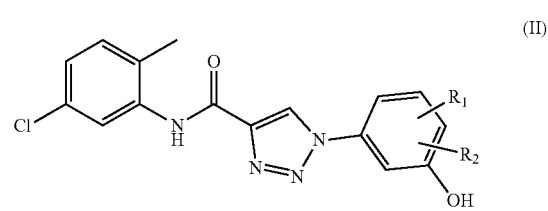

(II)

wherein $R_1$ is selected from the group of H, halogen, and $C_1$-$C_3$ alkyl;

and $R_2$ is selected from H, $CF_3$, and halogen;

with the proviso that at least one of $R_1$ and $R_2$ is halogen or $CF_3$.

Another embodiment provides a compound of Formula (II), or a pharmaceutically acceptable salt thereof, wherein $R_1$ is selected from the group of H, F, Cl, Br, and $C_1$-$C_3$ alkyl; and $R_2$ is selected from H, F, Cl, and Br; with the proviso that at least one of $R_1$ and $R_2$ is selected from the group of $CF_3$, F, Cl, and Br.

Another embodiment provides compound of Formula (II), wherein $R_1$ is F; and $R_2$ is selected from the group of H, methyl, F, Br, and Cl; or a pharmaceutically acceptable salt thereof.

Another embodiment provides compound of Formula (II), wherein $R_1$ is Cl; and $R_2$ is selected from the group of H, methyl, F, Br, and Cl; or a pharmaceutically acceptable salt thereof.

Still another embodiment provides a compound of Formula (II), wherein $R_1$ is Br; and $R_2$ is selected from the group of H, methyl, F, Br, and Cl; or a pharmaceutically acceptable salt thereof.

Another embodiment provides compound of Formula (II), wherein $R_1$ is F; and $R_2$ is H; or a pharmaceutically acceptable salt thereof.

Another embodiment provides compound of Formula (II), wherein $R_1$ is H; and $R_2$ is $CF_3$; or a pharmaceutically acceptable salt thereof.

Another embodiment provides compound of Formula (II), wherein $R_1$ is methyl; and $R_2$ is H; or a pharmaceutically acceptable salt thereof.

Another embodiment provides compound of Formula (II), wherein $R_1$ is Cl; and $R_2$ is H; or a pharmaceutically acceptable salt thereof.

Still another embodiment provides a compound of Formula (II), wherein $R_1$ is Br; and $R_2$ is H; or a pharmaceutically acceptable salt thereof.

A further embodiment provides a compound of Formula (II), wherein $R_1$ is F; and $R_2$ is selected from the group of H, F, and $CF_3$; or a pharmaceutically acceptable salt thereof.

Yet another embodiment provides a compound of Formula (II), wherein $R_1$ is F; and $R_2$ is selected from the group of H and F; or a pharmaceutically acceptable salt thereof.

Another embodiment provides a compound of Formula (III), or a pharmaceutically acceptable salt thereof:

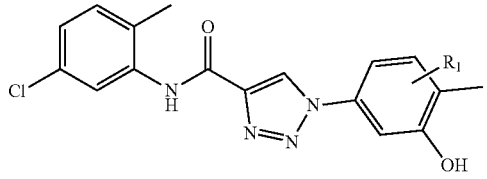

(III)

wherein $R_2$ is selected from $CF_3$ and halogen.

A further embodiment provides a compound of Formula (III), or a pharmaceutically acceptable salt thereof, wherein $R_2$ is selected from F and $CF_3$.

Excessive mitochondrial matrix $Ca^{2+}$ and oxidative stress leads to the opening of a high-conductance channel of the inner mitochondrial membrane referred to as the mitochondrial permeability transition pore (mtPTP). Because mtPTP opening can lead to cell death under diverse pathophysiological conditions (e.g. ischemia-reperfusion injury and muscular dystrophy,) inhibitors of mtPTP are potential therapeutics for various human diseases. High throughput screening efforts led to the identification of a 3-carboxamide-5-phenol-isoxazole compounds as mtPTP inhibitors. While they showed nM potency against mtPTP, they exhibited poor plasma stability, precluding their use in in vivo studies.

Herein, we describe a series of structurally related analogs in which the core isoxazole was replaced with a triazole, which resulted in an improvement in plasma stability. These analogs could be readily generated using the copper-catalyzed Huisgen cycloaddition reaction ("click chemistry"). One analog, N-(5-chloro-2-methylphenyl)-1-(4-fluoro-3-hydroxyphenyl)-1H-1,2,3-triazole-4-carboxamide (TR001), was efficacious in a zebrafish model of muscular dystrophy that results from mtPTP dysfunction whereas the isoxazole isostere had minimal effect.

Introduction

Cellular $Ca^{2+}$ metabolism and bioenergetics function as an integrated system, which is reflected by the mitochondrion's high capacity to store $Ca^{2+}$ in response to signals arising from elevation of cytoplasmic $Ca^{2+}$ [1,2]. While a number of specific mitochondrial $Ca^{2+}$ uptake and release pathways have been defined, the mitochondrial permeability transition pore (mtPTP) represents a unique kind of mitochondrial $Ca^{2+}$ release pathway. Indeed, this route of mitochondrial $Ca^{2+}$ release is characterized as voltage-dependent, cyclosporin A (CsA)-sensitive, high-conductance channel of the inner mitochondrial membrane (IMM) activated by mitochondrial accumulation of $Ca^{2+}$, but is not selective for $Ca^{2+}$ [3]. Many structurally unrelated compounds or conditions affect mtPTP transitions between its open and closed conformation, and the identification of numerous, discrete regulatory points strongly suggest a molecular structure of pronounced complexity [4-6]. Significantly, it became clear early on that mtPTP played a key role in a wide variety of human pathologies whose shared characteristics may be based in mitochondrial dysfunction triggered by $Ca^{2+}$ and potentiated by oxidative stress (e.g., [7]). However, our knowledge of the molecular composition of the mtPTP has been historically distracted by assumptions that had little experimental evidence and have subsequently been discounted from their participation in mtPTP formation through rigorous genetic analysis (e.g., [8]). More recently, a novel hypothesis proposes that the mtPTP forms from dimers of the $F_0F_1$ ATP synthase (ATP synthase) [9]. However, alternate models have been developed [10]; as a result, the identity of the proteins forming the mtPTP are currently debated.

Key insights in this and the mtPTPs critical participation in a variety of human therapeutic challenges would be advanced by the identification of agents with specifically inhibit, and therefore target, the mtPTP. Pharmacological agents targeting the mtPTP are generally restricted to compounds that target regulatory factors. For example CsA targets cyclophilin D (CyPD), an essential regulator of mtPTP [3]. An inherent limitation of CsA and other CyPD inhibitors is that these compounds are not mtPTP blockers, as demonstrated by the fact that the mtPTP can still open after genetic elimination of CyPD (e.g., [11]). Therefore, recently we identified several classes of compounds that specifically target the mtPTP using robust, high throughout mtPTP assays [12,13]. We identified several chemotypes that were optimized using medicinal chemistry efforts to yield, to our knowledge, the most potent mtPTP inhibitors thus reported. These mtPTP inhibitors—the most potent of which contain an isoxazole core—are efficacious at nanomolar concentrations, are non-toxic to mammalian cells and are beneficial in an animal model of a human muscular dystrophy caused, in part, by inappropriate mtPTP activation. However, plasma instability of the isoxazole-based mtPTP inhibitors proved detrimental for further in vivo studies. Thus, we sought improvement of plasma stability of these mtPTP inhibitors. Herein, we describe a new series of triazole-based mtPTP inhibitors that exhibit improved plasma stability. The synthesis of the triazole core of these inhibitors was accomplished using "click chemistry" of easily prepared aryl azides and aryl propynamides. The facile synthesis of the triazole mtPTP inhibitors allowed for thorough structure-activity relationship (SAR) studies. In a zebrafish model of muscular dystrophy caused by inappropriate mtPTP activation, the triazole-based inhibitor TR001 was more efficacious than the nearly identical isoxazole-based inhibitor 63.

Results and Discussion

Plasma Stability of First Generation mtPTP Inhibitors

The first generation of mtPTP inhibitors described by Roy et al. [12] contain a core heterocycle flanked by two aryl substituents. The most potent compound, 63, has isoxazole with a carboxamide at C-3 and an ortho substituted phenol group at C-5 (Table 1). While it exhibits nanomolar potency against mtPTP in vitro, it has a short half-life ($t_{1/2}$) in plasma ($t_{1/2}$ of 21 minutes, Table 1). Replacing the isoxazole with either a pyrazole (72) or an N-2-methyl pyrazole (73 and 74) improved plasma stability (Table 1), but unfortunately these compounds exhibited mitochondrial toxicity [12].

Synthesis of Triazole Analogs

Previous studies demonstrated that replacement of an isoxazole core with a triazole in TGR5 agonists resulted in a substantial improvement in pharmacokinetic properties [14]. Because we desire to develop mtPTP inhibitors with favorable pharmacokinetic profiles for in vivo studies, we designed and synthesized a series of second generation analogs of 63 in which the core isoxazole was replaced with a triazole. These analogs exhibit various substituents on the phenolic group at N-1 position of the triazole ring for exploring SAR on this side of the compounds.

The synthesis of these compounds is described in Scheme 1. Briefly, 1,3-Aminophenols 2a-i were purchased or synthesized from aryl nitro or aryl methoxy starting materials. These anilines were diazotized using a method adapted from Filimonov [15], then subsequently converted into aryl azides 3a-i using standard procedures. Aniline 4 was coupled to propiolic acid using standard DCC coupling procedures to afford the N-phenyl propiolamide 5. Finally, triazoles TR001-013 were synthesized readily by coupling the aryl azides 3a-l to N-phenyl propiolamide 5 using the copper(I)-mediated Huisgen cycloaddition reaction (commonly referred to as "click chemistry").

TABLE 1

Structure-activity relationships around the central five-membered ring. Effects on mouse plasma stability.

| Compound | Structure | Mouse Plasma $t^{1/2}$ (min) |
|---|---|---|
| TR001 | 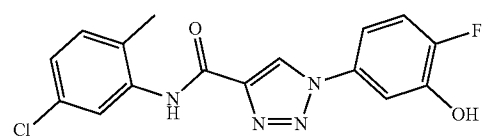 [SMILES: Cc1ccc(Cl)cc1NC(=O)c1cn(-c2ccc(F)c(O)c2)nn1] | 990 |
| 63[a] | 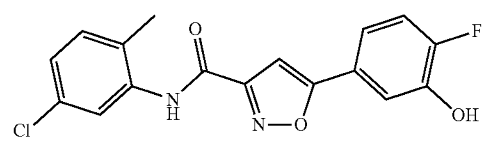 [SMILES: Cc1ccc(Cl)cc1NC(=O)c1cc(-c2ccc(F)c(O)c2)on1] | 21 |
| 72[a] | 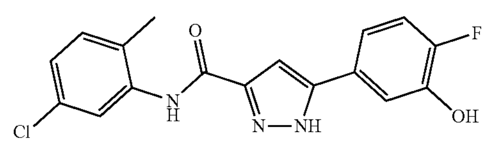 [SMILES: Cc1ccc(Cl)cc1NC(=O)c1cc(-c2ccc(F)c(O)c2)[nH]n1] | 533 |
| 73[a] | 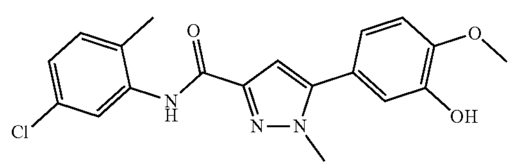 [SMILES: COc1ccc(-c2cc(C(=O)Nc3cc(Cl)ccc3C)nn2C)cc1O] | 85 |
| 74[a] | 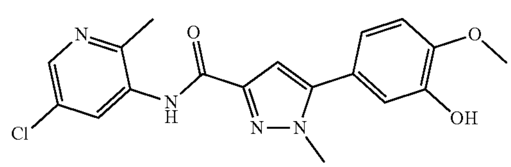 [SMILES: COc1ccc(-c2cc(C(=O)Nc3cc(Cl)cnc3C)nn2C)cc1O] | 151 |

[a]Compounds first reported by Roy et al., *ChemMedChem* 2015, 10, 1655-1671.

Initially, we evaluated the plasma stability of TR001. Compared to 63, TR001 exhibited a 47-fold increase in plasma stability (Table 1). This result demonstrates that substantial improvement in plasma stability can be achieved by simply replacing the isoxazole in 63 with a triazole.

Scheme 1. (a) Pd/C, HBF$_4$·Et$_2$O, H$_2$, MeOH; (b) 1—NaNO$_2$, HBF$_4$·Et$_2$O, AcOH, 2—NaN$_3$, H$_2$O, EtOAc; (c) BBr$_3$, DCM; (d) DCC, MeCN; (e) 3b-i, CuSO$_4$·5H$_2$O, sodium ascorbate, EtOH.

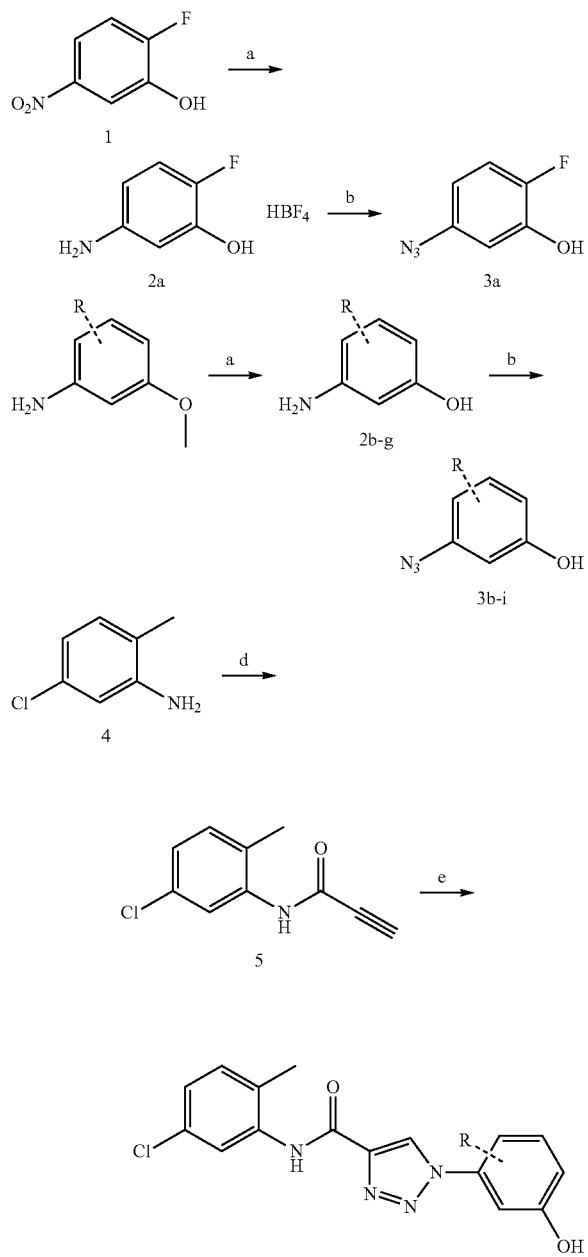

Structure-Activity Relationship Studies

We next sought to evaluate the effects of TR001-13 on mtPTP activity in vitro. This was performed on isolated mitochondria. In isolated mitochondria induction of mtPTP opening leads to mitochondrial swelling due to the oncotic pressure gradient created by matrix proteins >1.5 kDa that cannot diffuse through the open pore. In in vitro experiments, where isolated mitochondria are routinely suspended in sucrose-based isosmotic solutions, the change in mitochondrial size can be measured spectrometrically by detecting the decrease in light scattering at 540 nm.

Figure 1B:
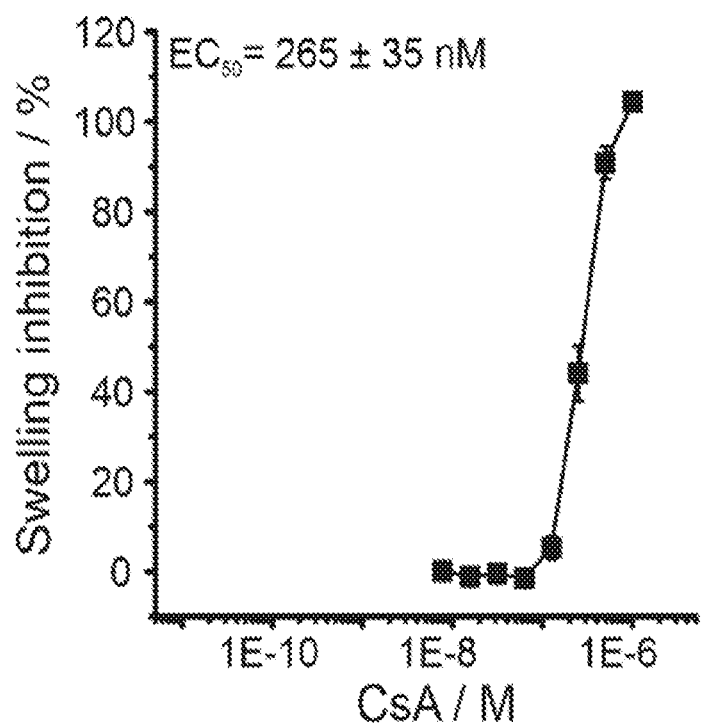
FIG. 1B graphs the percent of inhibition calculated at 20 min after $Ca^{2+}$ addition. Data are average±SEM of n=39 independent preparations.

First, we sought to confirm that a classical mtPTP inhibitor CsA prevents mitochondrial swelling in the expected concentration range in our mitochondrial preparations. We challenged isolated mouse liver mitochondria with 60 μm Ca$^{2+}$ to induce mtPTP opening in the presence of vehicle (DMSO) or increasing concentrations of CsA. As expected, CsA dose-dependently reversed the Ca$^{2+}$-mediated decrease in light scattering (EC$_{50}$ value of 265±35 nm) (FIGS. 1A, 1B).

Figure 1C:
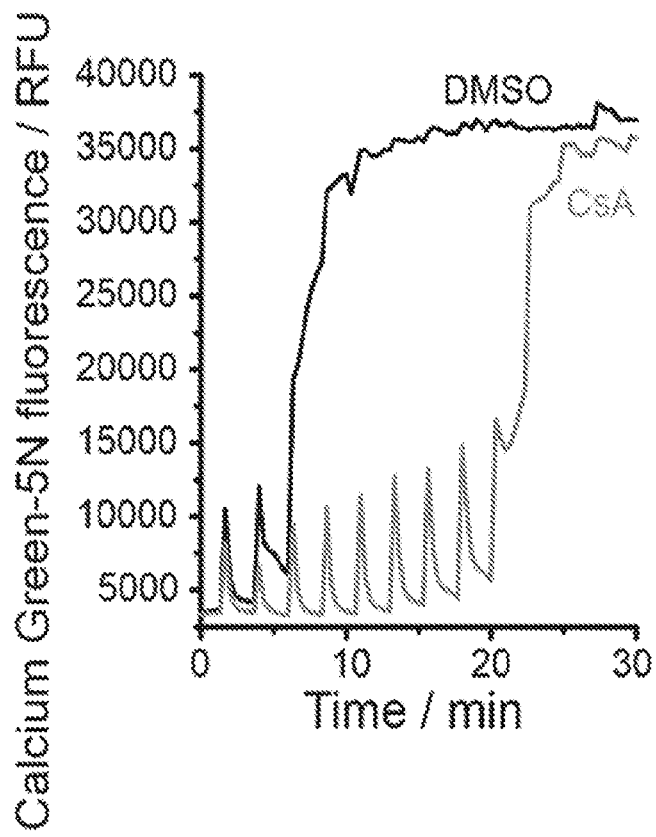
FIG. 1C graphs representative traces of calcium retention capacity (CRC) of vehicle (DMSO) or 1.25 μm CsA treated mouse liver mitochondria. Each spike of fluorescence represents 10 μm $Ca^{2+}$ injection.
Figure 1D:
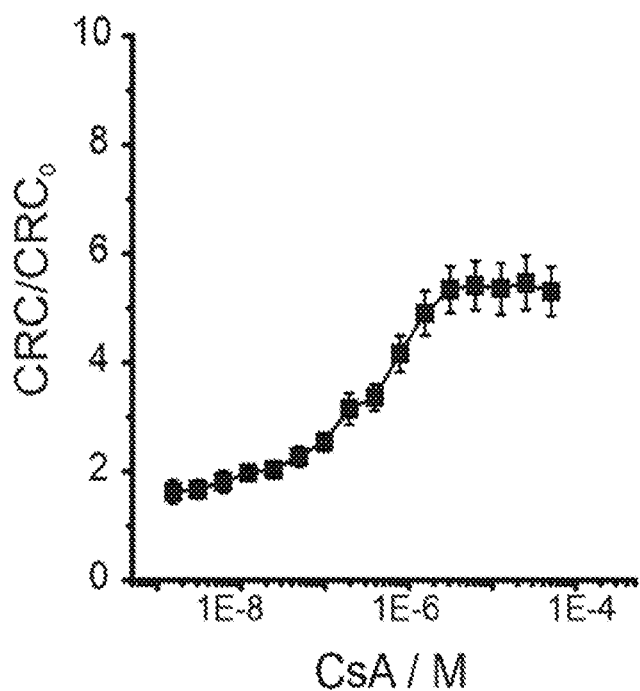
FIG. 1D graphs the concentration response of compound treated, CRC, to DMSO-treated, $CRC_0$, ratios, data are average±SEM of n=25 independent preparations.

Next, we used the Ca$^{2+}$ retention capacity (CRC) assay to validate the activity of CsA first and then of the newly synthesized mtPTP inhibitors reported here. CRC determines the Ca$^{2+}$ threshold required for mtPTP activation; inhibitors of mtPTP are expected to increase the Ca$^{2+}$ threshold required for mtPTP induction. Extramitochondrial Ca$^{2+}$ changes are detected using the membrane-impermeant Ca$^{2+}$ indicator, Calcium Green-5N. Consistent with previous studies, CsA increased the Ca$^{2+}$ load mitochondria could store before mtPTP opening (from ~70 to 320 nmol/mg protein), with a CRC ratio (drug-to-vehicle) of 4.6 at 1.25 μm CsA (FIG. 1C, 1D).

Figure 2:
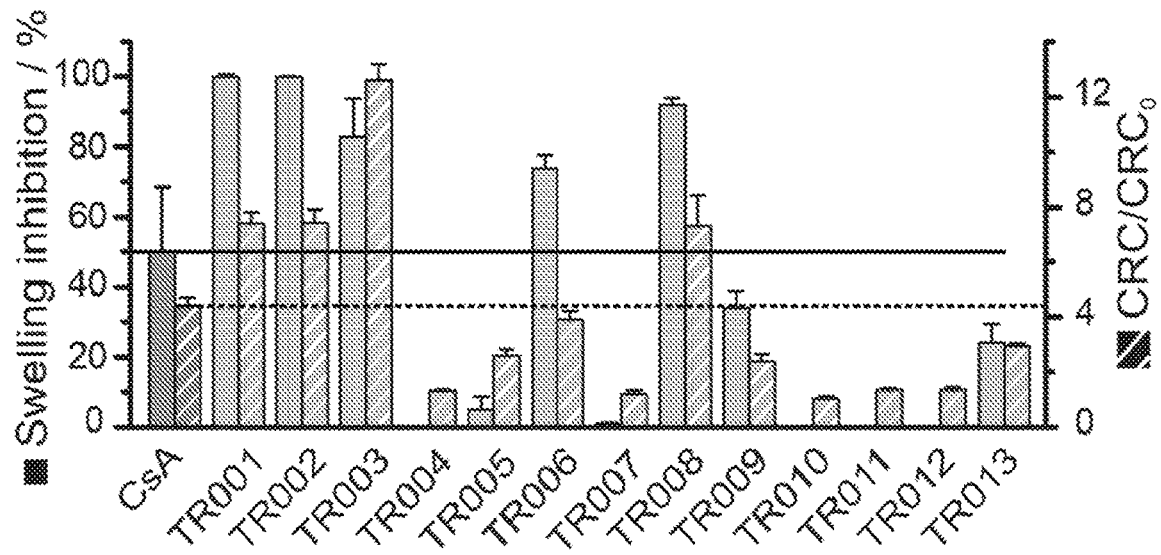
FIG. 2 provides a bar graph of triazole ranking against CsA, representing the percent of $Ca^{2+}$ overload induced mitochondrial swelling inhibition at 265 nm of indicated compounds; data are average±SEM of n=3-41 independent preparations.

We next determined the swelling EC$_{50}$ and CRC ratios for TR001-013 (FIG. 2 and Table 2). Out of 13 compounds tested 4 compounds showed superior activity, 1 comparable activity and 8 lower activity (or were inactive) compared to CsA (FIG. 2 and detailed below).

While the majority of the substituents on the phenolic ring of the isoxazole series [12] had been ortho to the hydroxyl group, it was unclear whether this was optimal for mtPTP inhibitory activity. Because of the readily available starting materials and facile synthetic route we developed for the triazole series, we could easily test the effects of ortho versus meta versus para substituents on the phenolic ring. A series of isobaric compounds were prepared which contain a fluorine at all three positions in the phenolic ring. The most potent analog was the meta substituted compound TR002 followed by ortho analog TR001 (Table 2).

Interestingly, the alternative ortho analog TR003 exhibited a 5-fold decrease in activity compared to TR001 and the para analog TR004 was inactive (Table 2). The difluoro analog TR005 with substitutions at both ortho positions exhibited decreased activity (Table 2). These results suggest that the position of the fluorine substituent can dramatically influence activity on mtPTP, and support very tight steric and electronic constraints on inhibitor binding to its target.

We also synthesized analogs that contain other substituents on the phenolic ring to further explore the SAR. Analogs of TR001 with either chlorine (TR006) or bromine (TR009) in the ortho had decreased activity and CRC/CRC$_0$ ratio compared to TR001 (Table 2). Similar results were found for the chlorine analog of TR002 (TR008) which exhibited a 2-fold decrease in activity compared to TR002 (Table 2). The methyl substituted analogs TR011 and TR012 were inactive, suggesting a preference for electron withdrawing groups on the phenolic ring. Interestingly, however, the trifluoromethyl analog TR013 had significantly reduced activity compared to either TR002 or TR008, suggesting that the steric bulk is a greater influence than its electron withdrawing properties.

TABLE 2
Structure-activity relationships of the phenolic ring built on the triazole core.
Effects on mtPTP inhibition and IMM potential.
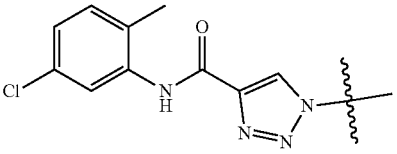 [SMILES: *n1cc(C(=O)Nc2cc(Cl)ccc2C)nn1]
| Compound | | Mitochondrial Swelling EC$_{50}$ (μM)[a] | CRC/CRC$_0$ at 1.25 μM[b] | Rh123 uptake EC$_{50}$ (μM)[c] |
|---|---|---|---|---|
| TR001 | 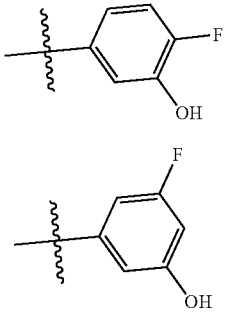 | 0.029 ± 0.008 | 6.8 ± 0.4 | >40 |
| TR002 | 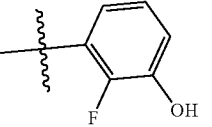 [SMILES: *c1cccc(O)c1F] | 0.010 ± 0.002 | 12.6 ± 0.6 | 14.1 ± 1.2 |
| TR003 | 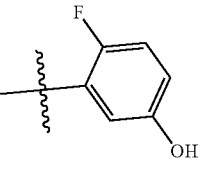 [SMILES: *c1cc(O)ccc1F] | 0.152 ± 0.036 | 7.4 ± 0.5 | 29.3 ± 3.3 |
| TR004 | 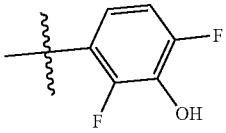 [SMILES: *c1ccc(F)c(O)c1F] | >20 | 1.3 ± 0.03 | >40 |
| TR005 | 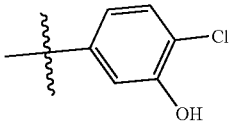 [SMILES: *c1ccc(Cl)c(O)c1] | 0.782 ± 0.114 | 2.6 ± 0.2 | >40 |
| TR006 | 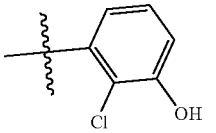 [SMILES: *c1cccc(O)c1Cl] | 0.135 ± 0.015 | 3.9 ± 0.3 | >40 |
| TR007 | 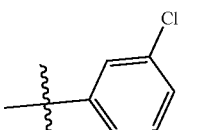 | >20 | 1.2 ± 0.1 | >40 |
| TR008 | 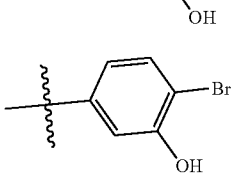 | 0.028 ± 0.005 | 7.3 ± 1.1 | >40 |
| TR009 |  | 0.475 ± 0.057 | 2.4 ± 0.2 | >40 |

TABLE 2-continued

Structure-activity relationships of the phenolic ring built on the triazole core.
Effects on mtPTP inhibition and IMM potential.

| Compound | Structure | Mitochondrial Swelling $EC_{50}$ (μM)[a] | $CRC/CRC_0$ at 1.25 μM[b] | Rh123 uptake $EC_{50}$ (μM)[c] |
|---|---|---|---|---|
| TR010 | 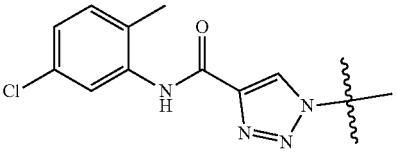 | >20 | 1.1 ± 0.1 | >40 |
| TR011 | 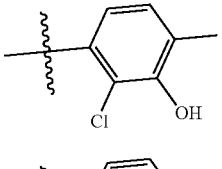 | >20 | 1.4 ± 0.1 | >40 |
| TR012 | 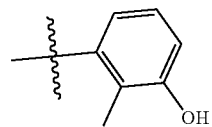 [SMILES: *c1cccc(O)c1C] | 10.6 ± 1.4 | 1.4 ± 0.1 | >40 |
| TR013 | 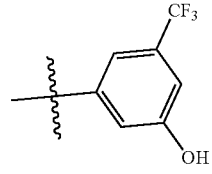 [SMILES: *c1cc(O)cc(C(F)(F)F)c1] | 0.534 ± 0.047 | 2.9 ± 0.1 | 6.2 ± 1.2 |

[a]Data are average ± SEM of n = 3-41 independent preparations.
[b]Compound treated mitochondrial calcium retention capacity (CRC) to DMSO treated ($CRC_0$) ratios. Data are average ± SEM of n = 3-25 independent preparations.
[c]Interference with rhodamine 123 (Rh123) uptake to mitochondria as a readout of interference with a buildup of inner mitochondrial membrane potential. Data are average ± SEM of n = 3 independent preparations.

We next evaluated the mitochondrial toxicity of the new triazole analogs by testing their ability to interfere with accumulation of the membrane-permeant cationic fluorescent dye rhodamine 123 (Rh123). The mitochondrial uptake of positively charged Rh123 is driven by the inside negative IMM potential, which is built by the respiratory chain or maintained by ATP hydrolysis if certain conditions are met. The majority of triazoles does not interfere with the buildup of IMM potential except for TR002, TR003 and TR013 (Table 2). Hence the position and nature of the substituent on the phenolic ring can influence mitochondrial toxicity. It should be noted, however, that toxicity for these compounds only occurs at ~10-1000-fold higher concentrations compared to mtPTP inhibition, providing a good therapeutic window.

TR001 is a Potent Inhibitor of the mtPTP

Based on the SAR studies and mouse plasma stability data, we decided to move forward with TR001 for more extensive biological characterization. As noted above, mtPTP is triggered by elevated levels of matrix $Ca^{2+}$ and potentiated by oxidative stress, leading to mitochondrial swelling. We therefore next tested the ability of TR001 to protect from oxidizing agent-triggered mtPTP opening. For this purpose, we used known chemical activators of the mtPTP that react with two distinct classes of redox sensitive thiols (—SH) and increase the propensity of mtPTP opening.

Figure 3A:
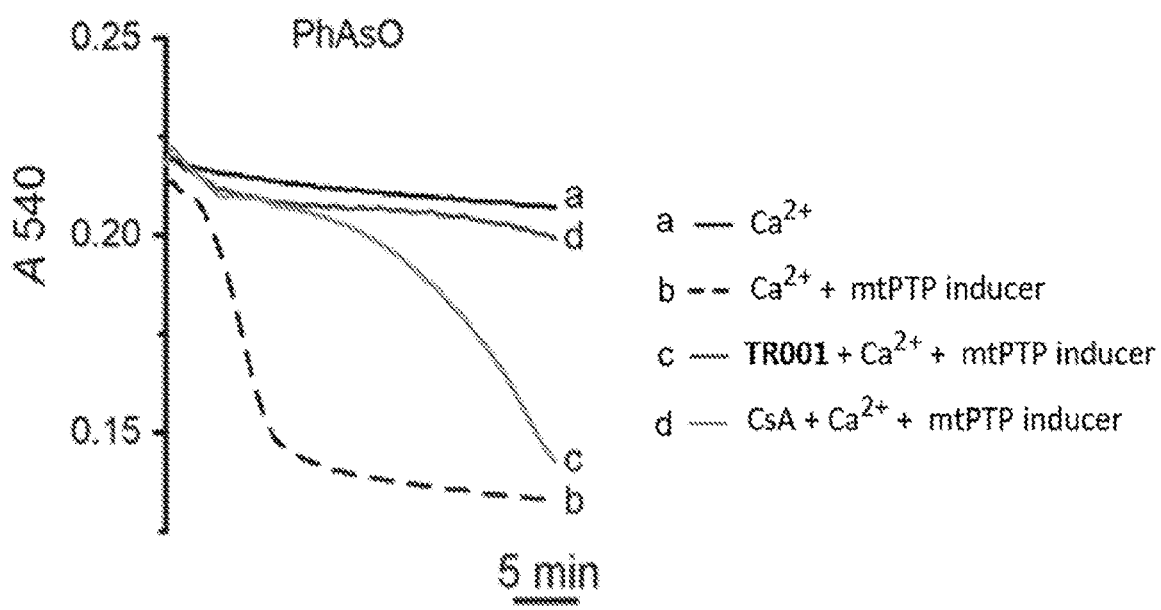
Figure 3B:
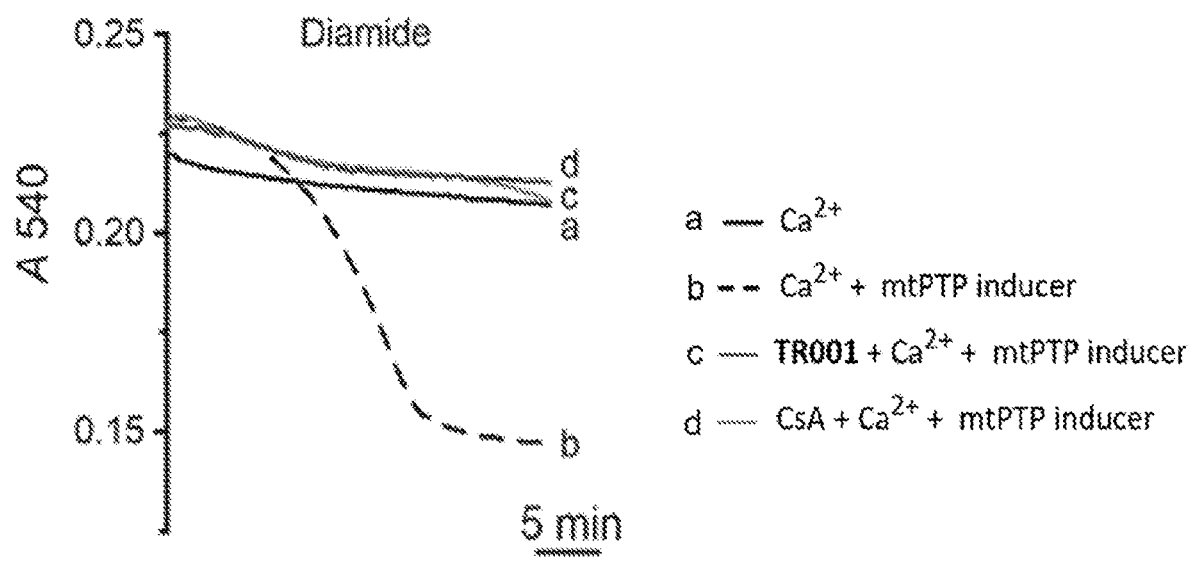
Figure 3C:
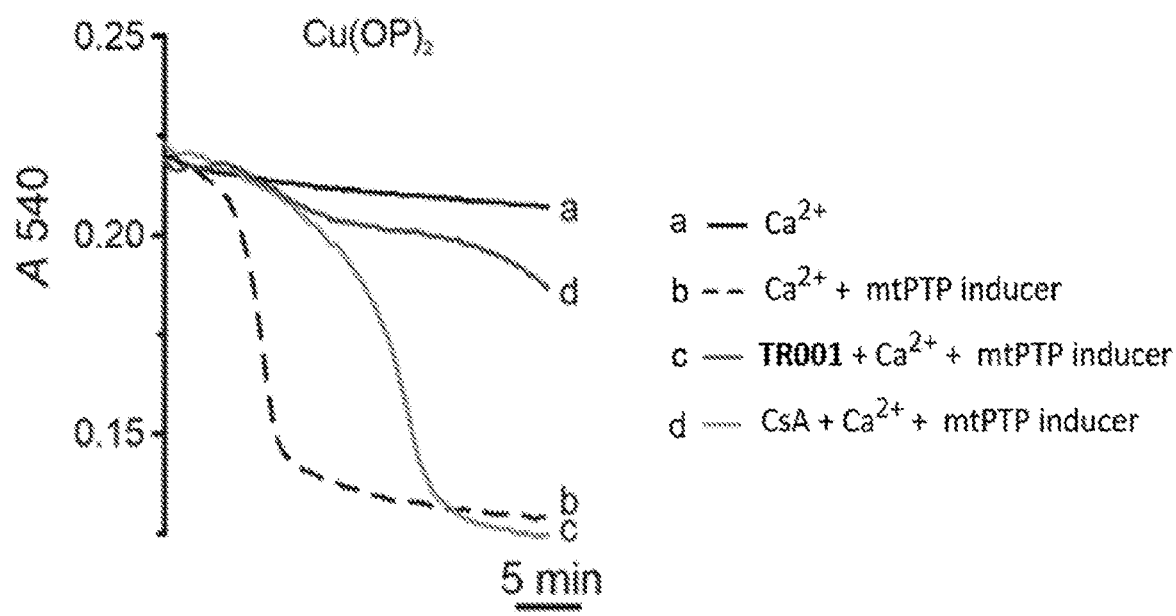
Figure 3D:
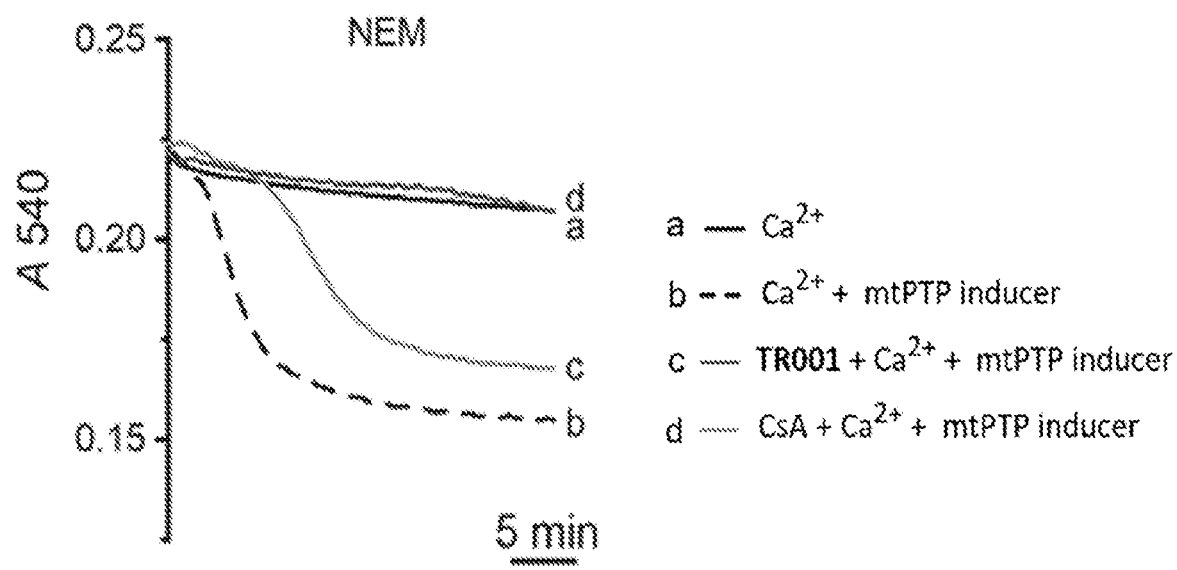

We first pretreated energized isolated mouse liver mitochondria with 10 μm $Ca^{2+}$, amount insufficient to induce mtPTP opening per se (FIGS. 3A-3D, traces a), and then added (i) phenylarsine oxide (PhAsO) or Diamide (FIGS. 3A and 3B, respectively), reagents primarily reacting with matrix thiols [16] or (ii) copper-o-phenanthroline (Cu(OP)$_2$) and mm concentrations of N-ethylmaleimide (NEM) (FIGS. 3C and 3D, respectively), reagents reacting with intermembrane space exposed thiols [17,18], to induce mtPTP transition from a closed to open conformation, see traces b. In this experimental setting a set of samples was treated either with 1.5 μm CsA or 1.5 μm TR001 prior to $Ca^{2+}$ and oxidant addition. In all cases both CsA and TR001 delayed mtPTP opening, with TR001 being much more effective than CsA.

CyPD is not a Target of TR001

Figure 4A:
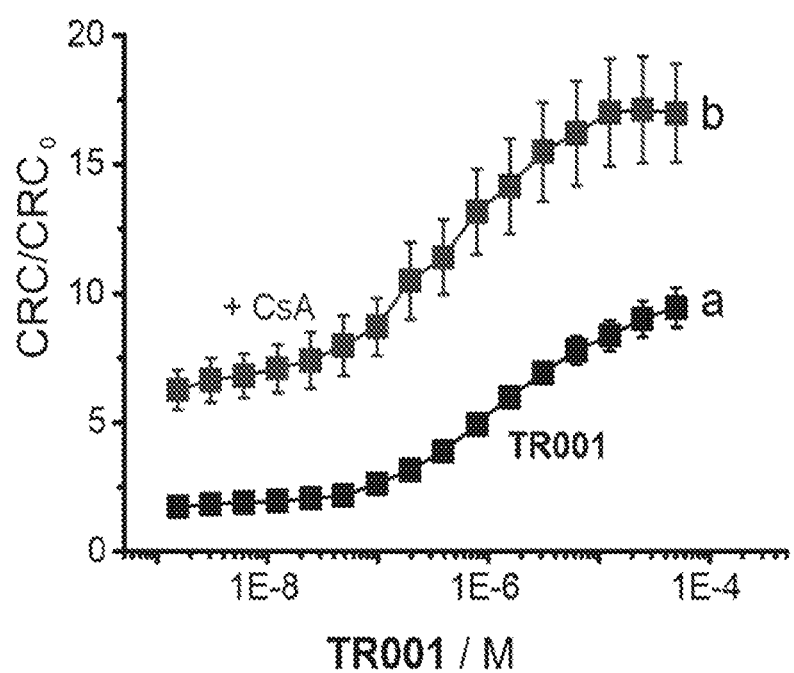
FIGS. 4A-4B graphs compound TR001 inhibition of the mtPTP independently of CyPD.
Figure 4B:
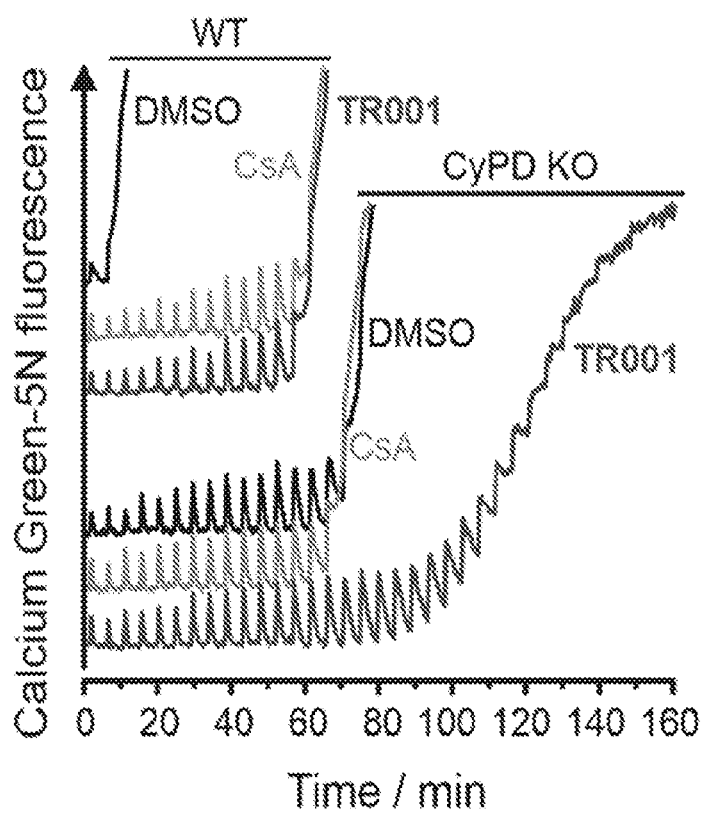

The above experiments demonstrate that TR001 is a more potent mtPTP inhibitor than CsA. Given that the maximal efficacy as defined by $CRC/CRC_0$ ratio is ~10 for TR001, twice as much as for CsA, suggests that TR001 might act on a different target than CsA. Consistent with this notion, we found that TR001 was additive with CsA (FIG. 4A). To further determine if TR001 acts on CyPD,—the target of CsA,—we performed the CRC test in permeabilized WT or CypD-null HEK 293T cells. In contrast to CsA, which had no effect on CypD-null cells, TR001 increased the CRC in both WT and CyPD-null cells FIG. 4B). Taken together, these results demonstrate that CyPD is likely not the target of TR001.

TR001 does not Affect Mitochondrial or Cultured Cell Health

Figure 5A:
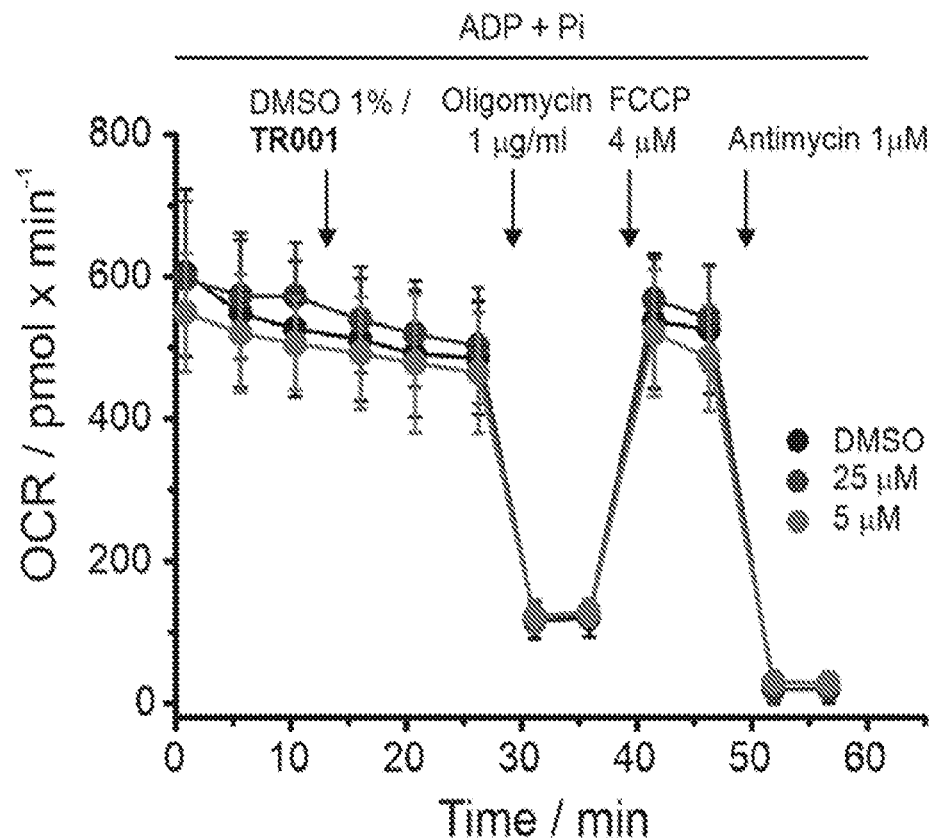
FIGS. 5A-5D demonstrate that TR001 is not toxic to either mitochondria or intact cells. Oxygen consumption rates (OCR) of isolated mitochondria, FIG. 5A, or HeLa cell monolayers, FIG. 5C, were measured in the presence of indicated concentrations of TR001. Traces are representative of 4 and 5 separate experiments, respectively.
Figure 5B:
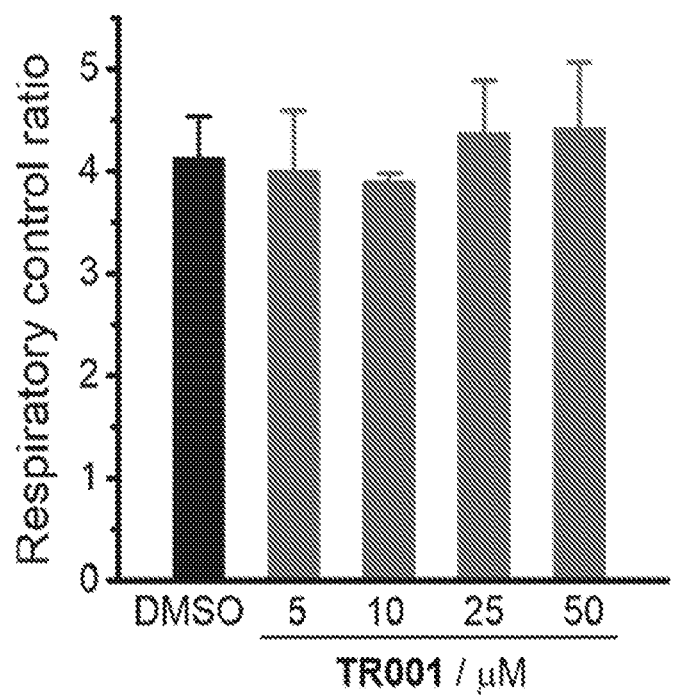
Figure 5C:
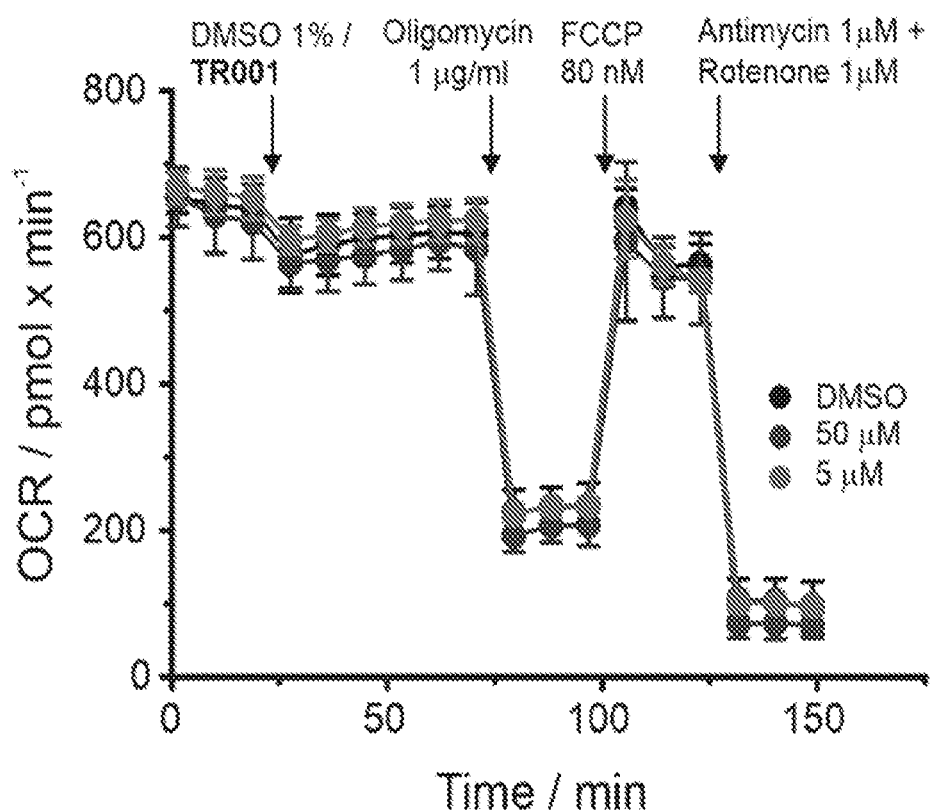
Figure 5D:
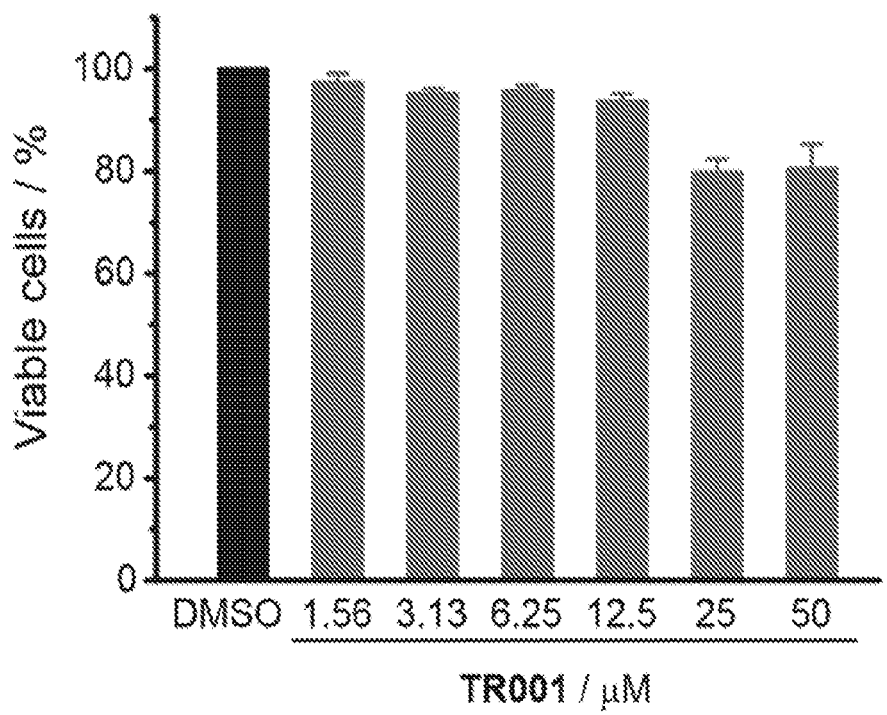

A thorough evaluation of toxicity is critical for advancing TR001 to in vivo studies. Initial assessment using the Rh123 uptake assay showed that TR001 did not interfere with IMM potential. To more thoroughly examine mitochondrial toxicity, we analyzed oxygen consumption rates (OCRs) using the Seahorse XF24 extracellular flux analyzer. This allowed us to assess the effects of TR001 on mitochondrial respiration and ATP synthesis. We found that TR001 had no effect on rates of oxygen consumption upon ADP stimulation (ATP production), after ATP synthase inhibition with oligomycin (basal respiration) or uncoupling with FCCP (maximal respiratory capacity) in isolated mitochondria (FIG. 5A). Consequently respiratory control ratios (i.e., the ratios between ADP-stimulated and basal respiration) were not affected across the concentrations tested (FIG. 5B). Complex III inhibitor antimycin A shuts down the electron transport chain at the bc1 complex and was used to account for oxygen leak. Similar results were obtained in intact cells (i.e., TR001 did not cause mitochondrial dysfunction in the course of ~2 h treatment) (FIG. 5C). Finally, TR001 (up to 50 μm) did not exhibit any adverse effects on HeLa cell viability (FIG. 5D Together, these results demonstrate that the TR001 is not toxic to mitochondria or cells.

Assessment of the Therapeutic Potential of TR001 in a Vertebrate Model of mtPTP-Based Disease Long-lasting opening of the mtPTP, probably due to mitochondrial $Ca^{2+}$ overload [19], is a common downstream mechanism during the pathogenesis of several muscular dystrophies, like Ullrich Congenital Muscular Dystrophy (UCMD). This is a dominant life-threatening disorder caused by mutations in genes encoding collagen VI. These mutations result in defective or absent collagen VI, an essential component of extracellular matrix in skeletal muscle. Mouse models of UCMD with knock-outs for the murine Col6a1 gene exhibit relatively mild phenotypes when compared to those observed in humans. However, it is widely documented that inappropriate mtPTP activity, both in humans and mice, plays a key role in disease pathogenesis [20-22]. Desensitization of the mtPTP both in mice and human cell lines, using either pharmacological treatment with CyP inhibitors (CsA and its non-immunosuppressive derivatives) [20,23] or elimination of the Ppif gene encoding CyPD [21] were found to restore normal mitochondrial function and to decrease myofiber cell death. An additional model of UCMD has been generated in zebrafish through the injection of an antisense morpholino oligonucleotide directed to the exon 9 splicing region of the human orthologous col6a1 gene in zebrafish, resulting in an in-frame deletion mimicking common mutations in human UCMD [24,25]. Morpholino-injected animals (morphants) developed a severe myopathy which accurately mimicked the clinical severity of human UCMD with early-onset motor deficits and severe muscular and mitochondrial ultrastructural changes. This severe phenotype was reversed by treatment with non-immunosuppressive derivatives of CsA [25]. Thus, we used the zebrafish col6a1 myopathic morphant as a powerful in vivo system to validate the therapeutic potential of TR001 and compared it to the isoxazole compound 63 which exhibits similar potency to TR001, but substantially decreased plasma stability (Table 1).

Figure 6A:
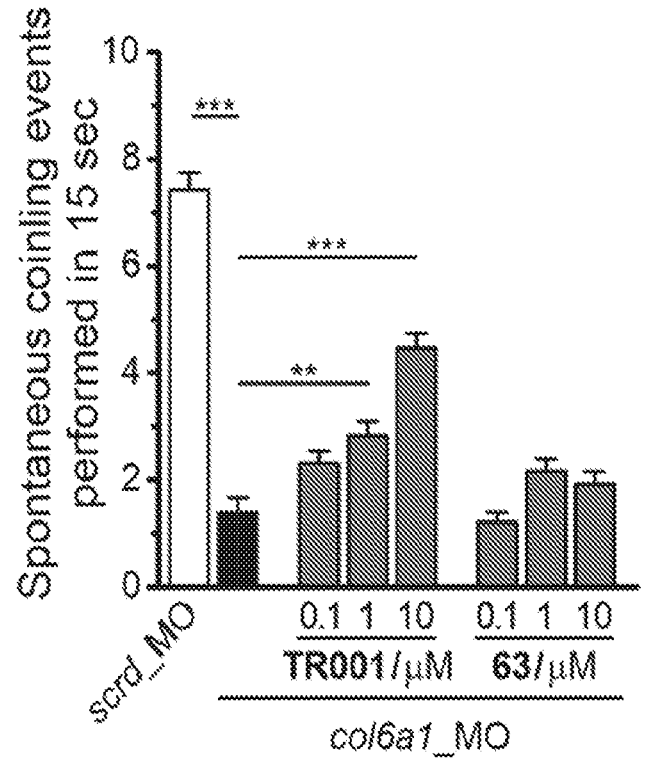
FIGS. 6A-6E chart effects of compounds TR001 and 63 treatment on col6a1 zebrafish morphants.
Figure 6B:
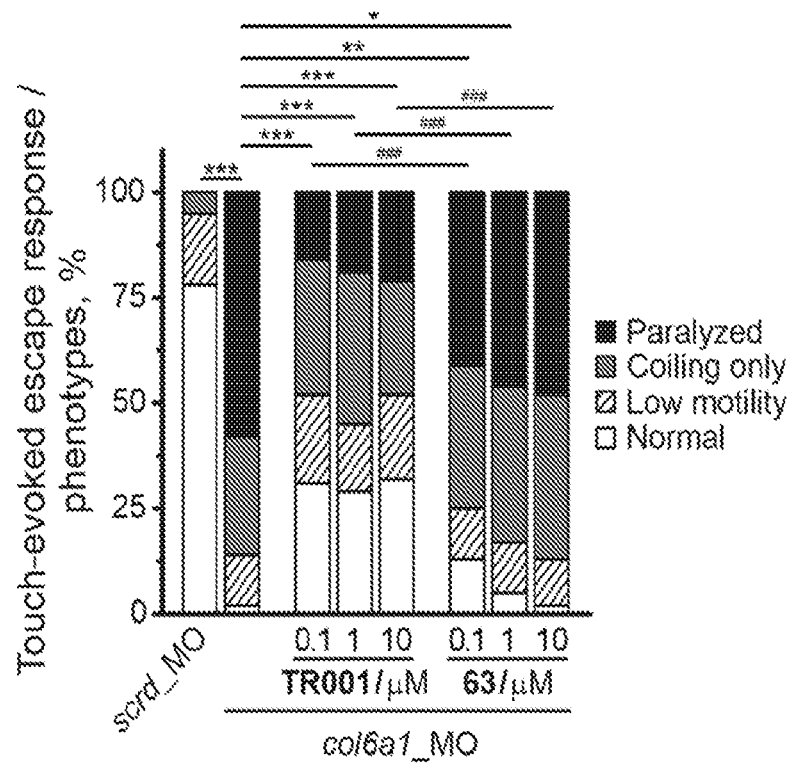

Zebrafish embryos were injected with col6a1 morpholino at the 1-cell stage, dechorionated at 20 hpf and treated at 21 hpf with 0.1, 1 or 10 μm of either TR001 or 63. DMSO-treated embryos injected with a scrambled morpholino were used as a control. Spontaneous coiling events were monitored at 24 hpf after 3 hours of treatment. col6a1 morphants exhibited a striking decrease in the number of spontaneous coiling events compared to zebrafish injected with a scrambled morpholino and treated with vehicle (FIG. 6A). Treatment with TR001 partially rescued the defect observed in col6a1 morphants in a dose-dependent manner; in contrast, 63 had no effect (FIG. 6B). Touch-evoked escape responses were recorded at 48 hpf, i.e., after 27 hours of treatment. col6a1 morphants showed a severely reduced motility, which was improved by treatment with TR001. By contrast, 63 caused minimal recovery at 0.1-1.0 μM, an effect that was no longer seen at 10 μm (FIG. 6B). It should be noted that in these protocols, embryos were exposed to drugs for a longer period of time than in the spontaneous coiling experiments. This difference may help to explain why TR001 was as effective at 0.1 μm as it was at 1 and 10 μm.

Figure 6C:
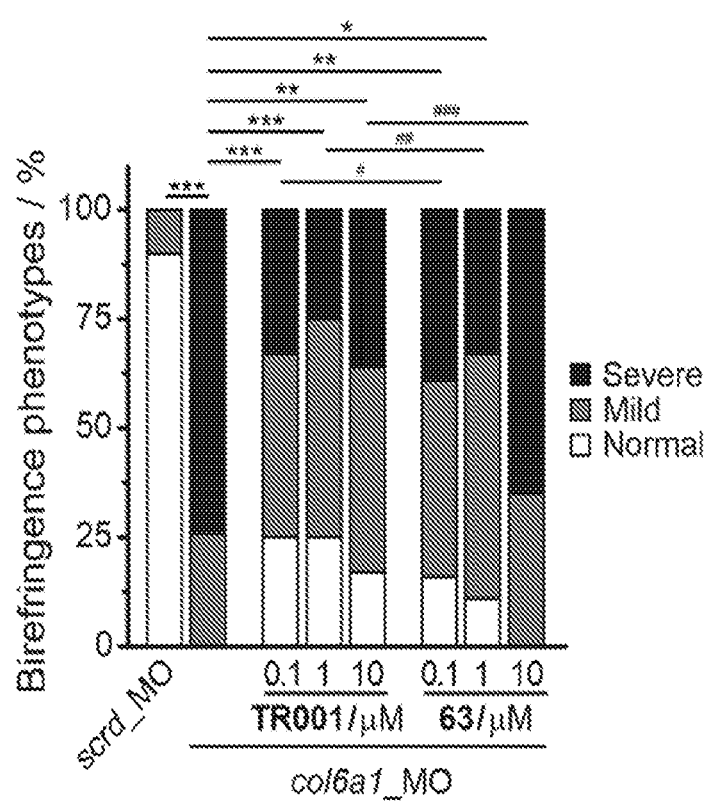

Muscle structure was assessed by birefringence analysis at 48 hpf, a time when muscle tissue is fully developed and organized muscle fibers start to show anisotropic features. A high percentage of severe birefringence abnormality (>75%, FIG. 6C) was detected in col6a1 morphants, indicating major defects of muscle fiber development and organization. TR001 significantly rescued col6a1 morphants from the defect in muscle structure whereas 63 exhibited a minimal effect (FIG. 6C).

Figure 6D:
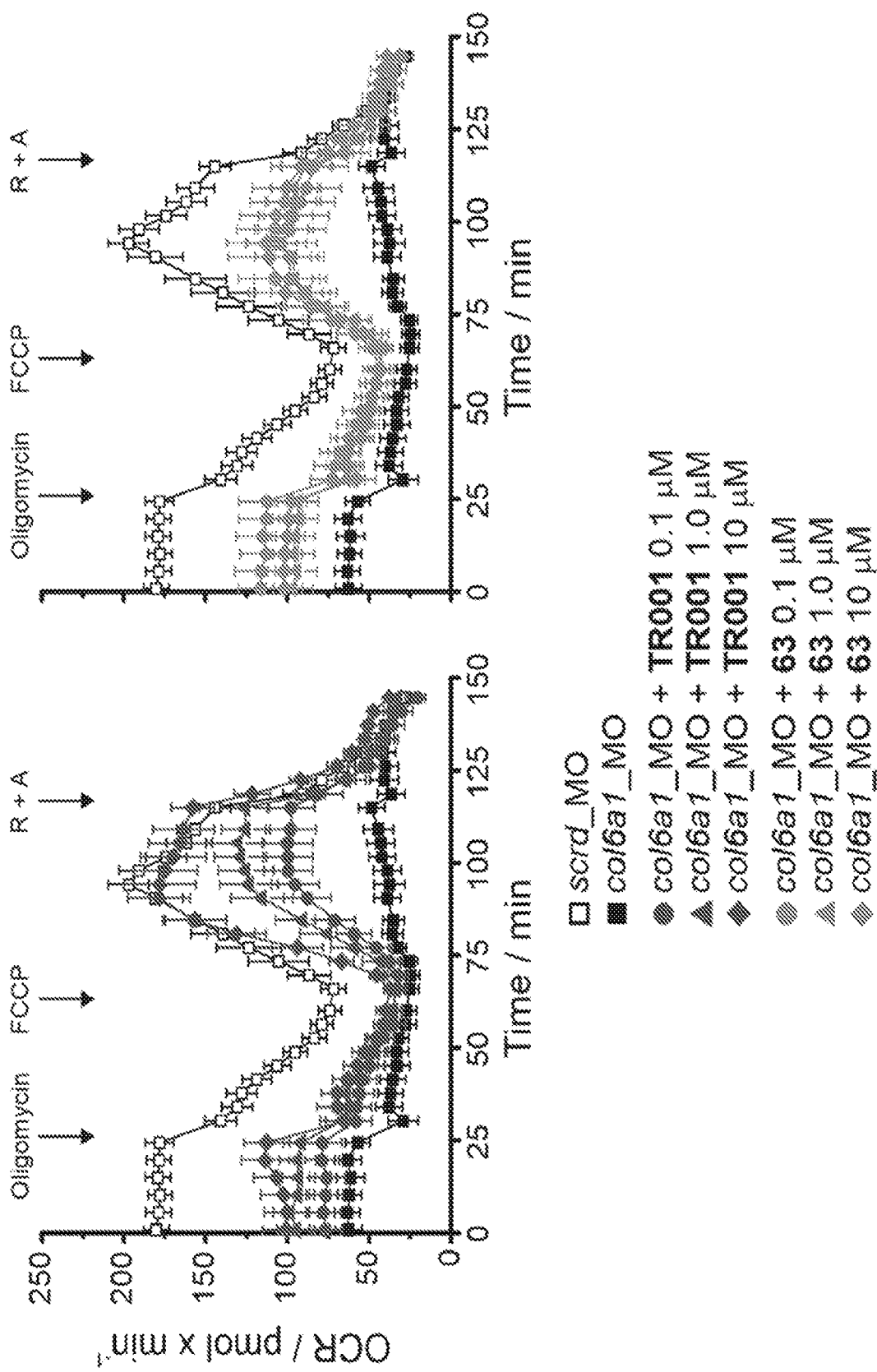

To test the effects of both TR001 and 63 on the respiration of col6a1 morphant embryos, we measured the OCR on entire embryos at 48 hpf. Sequentially, we measured (i) the basal respiration, (ii) the coupled respiration through the addition of 10 μm oligomycin which inhibits the activity of ATP Synthase, (iii) the maximal respiratory capacity by adding 2 μm of the uncoupler FCCP, (iv) the mitochondrial respiration after the inhibition of Complexes I and III by adding 1 μm rotenone and 1 μm antimycin A. We found that respiration of col6a1 morphants (closed squares) was significantly lower (p<0.001) than that of embryos injected with scrambled morpholino (open squares) (FIG. 6D). Moreover, TR001 at a concentration of 10 μm was able to fully restore the maximal respiratory capacity (FIG. 6D, left panel, open diamonds, p<0.001) of col6a1 morphants. In general, TR001 at all concentration used (FIG. 6D, left panel) was more effective than 63 (FIG. 6D, right panel).

Figure 6E:
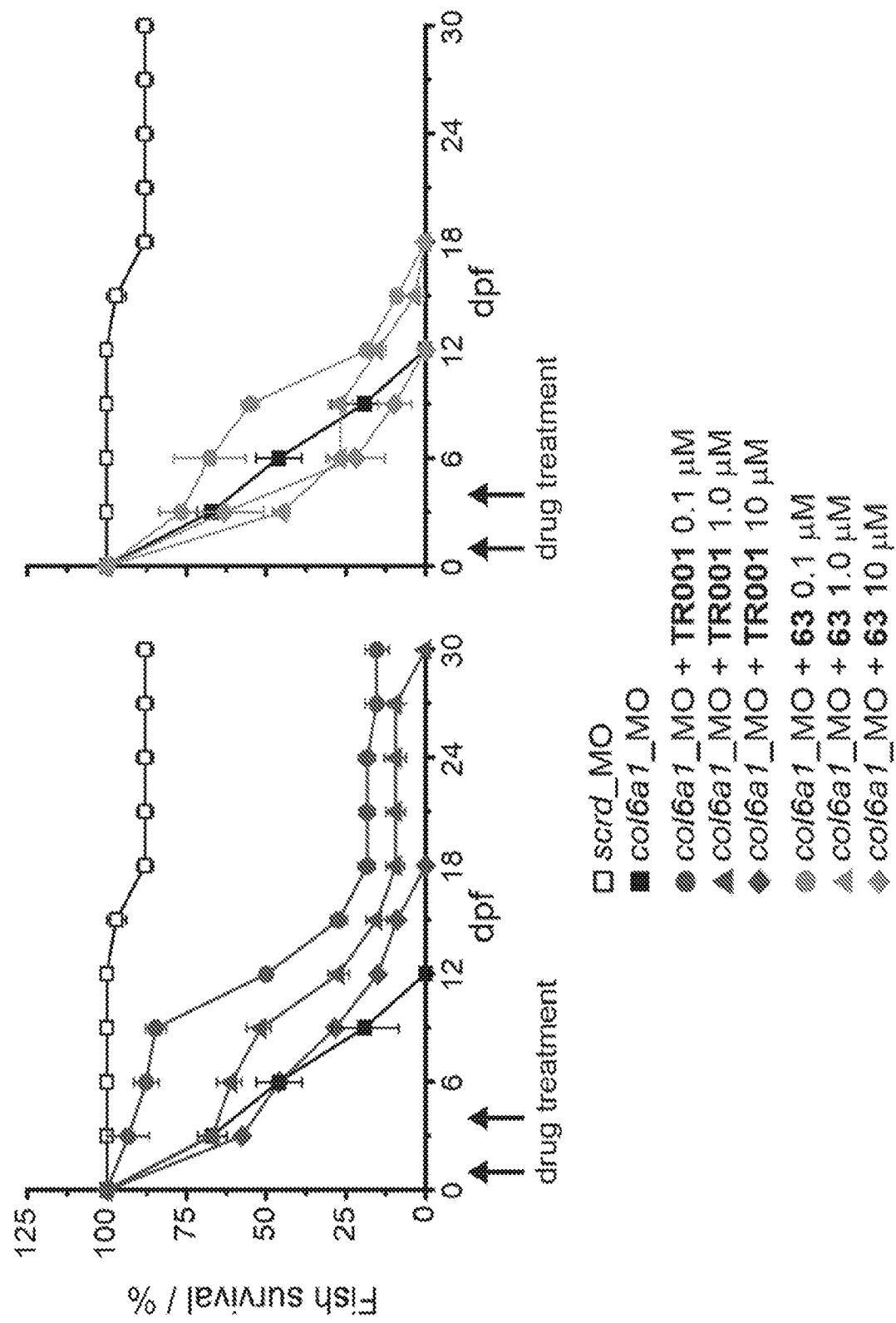
Figure 7:
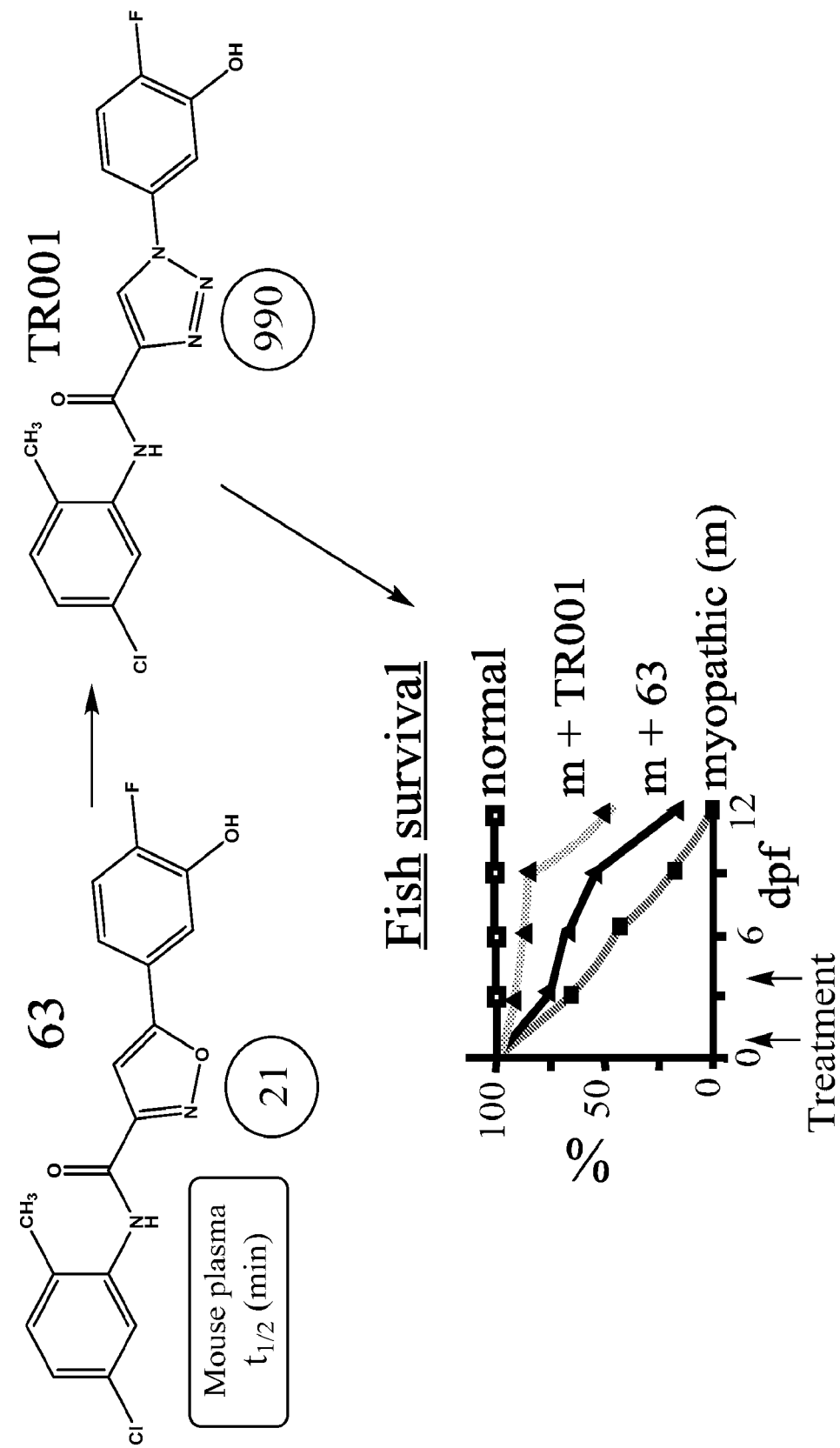
FIG. 7 represents graphically the effect of Compounds 63 and TR001 on fish survival post-treatment.

In FIG. 6D, the left panel represents data from embryos injected with a scrambled morpholino (scrd_MO, open squares), Exon 9 col6a1 morpholino (col6a1_MO, closed squares) and col6a1_MO embryos treated with TR001 at 0.1 μm (open circles), 1.0 μm (open triangles), 10 μm (open diamonds). Right panel represents data from embryos injected with a scrambled morpholino (scrd_MO, open squares), Exon 9 col6a1 morpholino (col6a1_MO, closed squares) and col6a1_MO embryos treated with 63 at 0.1 μmM (closed circles), 1.0 μm (closed triangles), 10 μm (closed diamonds). Embryos were treated with oligomycin, FCCP, rotenone (R) and antimycin A (A) as indicated. Results are presented as mean±SEM. Both graphs report data from 5 independent experiments with n=20 for each treatment. Error bars are reported as SEM. FIG. 6E, Survival of DMSO-treated zebrafish injected with the scrambled morpholino (open squares), DMSO-treated col6a1 morphants (closed squares) and col6a1 morphants treated with TR001 (0.1 μm, open triangles; 1.0 μm, open circles; 10 μm, open diamonds) or 63 (0.1 μm, closed triangles; 1.0 μm, closed circles; 10 μm, closed diamonds) were recorded for 30 days. Treatment started at 21 hpf and repeated at 4 dpf (arrows). Data report the percentage of surviving fish and are mean±SEM from 3 independent experiments (n=15 for each condition in each set).

Finally, fish survival was also assessed. Fifty percent of col6a1 morphant embryos treated with 0.1 µm of TR001 survived 7 days longer than col6a1 morphants treated with DMSO (p<0.0001 from 3 to 12 dpf), and 20% were still alive at 30 dpf (i.e., after 29 days of treatment) (FIG. 6E). Treatment with 1 µm TR001 was also effective at improving survival rate of col6a1 morphants (p<0.01 from 3 to 12 dpf), while 10 µm TR001 was ineffective. The lowest concentration of 63 tested showed decreased activity compared to TR001 and the rest were ineffected (FIG. 6E).

Conclusions

Exhaustive screens of small molecule libraries and the iterative development of those hits have resulted in the identification of the most potent mtPTP inhibitors reported to date. However, pharmacokinetic profiling found limitations in the first generation isoxazole-based scaffolds, precluding their use in in vivo studies. In this study, we overcame this deficit by replacing the core isoxazole with a triazole, which resulted in a compound (TR001) with improved plasma stability while maintaining potent mtPTP inhibition. Because the triazole analogs could be generated in a facile manner, we were able to perform SAR studies focused on the effects of substituents on phenolic ring at N-1 of the triazoles. These studies revealed a tight SAR, with a preference for a fluorine at the ortho or meta position of the phenolic ring. The tight SAR suggests that the phenolic ring projects into a well-defined pocket on a yet-to-be-identified target. The SAR studies performed in this study will guide the development of analogs for target identification. Finally, we demonstrated in an animal model of a muscular dystrophy based on dysregulation of the mtPTP the triazole TR001 is more efficacious than the sterically equivalent isoxazole 63. Our studies guide the further development of these compounds as potential therapies for a wide variety of human pathologies in which dysfunction of the mtPTP plays a key role.

Experimental Section

Chemistry 5-amino-2-fluorophenol tetrafluoroborate. 1 (2.5 g, 16 mmol) was dissolved in 80 mL of EtOH. Tetrafluoroboric acid etherate (4.35 mL, 32 mmol) and Pd/C (10% w/v, 0.25 g) were added, then the mixture was placed under a hydrogen atmosphere (20 psi) for 18 hr with shaking. The Pd/C was removed by filtration over celite, then the solution was concentrated to give 3.357 g of 2a (98% yield). $^1$H NMR (d$_6$-DMSO) δ 10.49 (s, 1H); 9.64 (s, 3H); 7.25 (q, 1H); 6.93 (q, 1H); 6.73 (m, 1H).

5-azido-2-fluorophenol. 2a (1.655 g, 7.7 mmol) was dissolved in 15 mL of AcOH. Tetrafluoroboric acid etherate (2.62 mL, 19.2 mmol) was added, followed by sodium nitrite (0.8 g, 11.5 mmol) in three portions over 30 min. The mixture was added dropwise to 150 mL of vigorously stirring Et$_2$O at 0° C. The resulting light brown precipitate was collected by filtration, then used in the next step without further purification. Sodium azide (5 g, 77 mmol) was dissolved in 77 mL of H$_2$O at 0° C. The diazonium from step 1 was added and stirred for 15 min at 0° C. The reaction was extracted 3× with 25 mL of EtOAc. The organic fractions were combined, washed 2× with 10 mL of brine, then dried with MgSO$_4$, filtered, and concentrated to give 0.97 g of 3a (82% yield). $^1$H NMR (d$_6$-DMSO) δ 10.28 (q, 1H); 7.18 (m, 1H); 6.66 (q, 1H); 6.54 (m, 1H).

General procedure for BBr$_3$ demethylation. A flask was loaded with molecular sieves (3 Å) and flame dried under vacuum. After cooling under argon, starting methyl ether (2 mmol) was loaded, followed by 10 mL of dry DCM. The flask was sealed and degassed, then the solution was cooled to −78° C. BBr$_3$ (0.9 mL, 10 mmol) was added dropwise, then the reaction was stirred for 18 hr to RT. The reaction was decanted into excess aqueous sat. sodium bicarbonate, then extracted 3× with 20 mL of EtOAc. The organic fractions were combined, washed 2× with 20 mL of brine, then dried with MgSO$_4$, filtered, and concentrated to give product in 20% to quantitative yield.

3-amino-2-fluorophenol (2b). Quant. yield. $^1$H NMR (CDCl$_3$) δ 6.81 (m, 1H); 6.38 (m, 2H); 5.02 (s, 1H); 3.75 (s, 2H).

3-amino-5-fluorophenol (2c). 20% yield. $^1$H NMR (d$_6$-DMSO) δ 9.28 (s, 1H); 5.81 (d, 1H); 5.78 (dt, 1H); 5.68 (dt, 1H); 5.25 (s, 2H).

5-amino-2-bromophenol (2d). 74% yield. $^1$H NMR (CDCl$_3$) δ 7.19 (d, 1H); 6.39 (d, 1H); 6.20 (dd, 1H); 5.39 (s, 1H); 3.72 (s, 2H).

3-amino-2-chlorophenol (2e). Quantitative yield. $^1$H NMR (CDCl$_3$) δ 6.98 (t, 1H); 6.45 (dd, 1H); 6.38 (dd, 1H); 5.44 (s, 1H); 4.05 (s, 2H).

3-amino-5-chlorophenol (2f). 55% yield. $^1$H NMR (d$_6$-DMSO) δ 9.32 (s, 1H); 6.02 (d, 1H); 5.92 (d, 2H); 5.27 (s, 2H).

3-amino-5-(trifluoromethyl)phenol (2g). Quantitative yield. $^1$H NMR (d$_6$-DMSO) δ 9.80 (s, 1H); 6.73 (s, 2H); 6.46 (s, 1H); 6.39 (s, 1H); 6.53 (s, 1H).

3-amino-2,6-difluorophenol (2h). 87% yield. $^1$H NMR (d$_6$-DMSO) δ 9.67 (s, 1H); 6.67 (m, 1H); 6.15 (m, 1H); 4.87 (s, 2H).

(2b)

(2c)

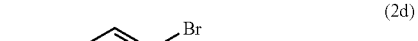

(2d)

(2e)

-continued (2f)
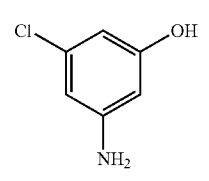

(2g)
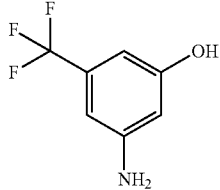

(2h)
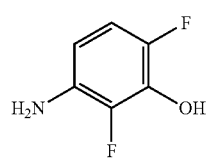

General procedure for aryl azide formation. Aniline (2 mmol) was dissolved in 4 mL of AcOH. Tetrafluoroboric acid etherate (0.8 mL, 6 mmol) was added, followed by sodium nitrite (0.2 g, 3 mmol) in three portions over 30 min. The mixture was added dropwise to 40 mL of vigorously stirring Et$_2$O at 0° C. The resulting light brown precipitate was collected by filtration, then used in the next step without further purification. Sodium azide (0.13 g, 4 mmol) was dissolved in 20 mL of H$_2$O at 0° C. The diazonium from step 1 was added, followed by the addition of 20 mL of EtOAc, then the reaction was stirred to RT over 18 hr. The reaction was extracted 3× with 25 mL of EtOAc. The organic fractions were combined, washed 2× with 10 mL of brine, then dried with MgSO$_4$, filtered, and concentrated.

3-azido-5-fluorophenol (3b). 76% yield. $^1$H NMR (D$_6$-acetone) δ 9.57 (s, 1H); 6.39 (m, 3H).

3-azido-4-fluorophenol (3c). 71% yield. $^1$H NMR (CDCl$_3$) δ 6.98 (t, 1H); 6.56 (m, 2H); 4.87 (s, 1H).

5-azido-2-chlorophenol (3d). 62% yield. $^1$H NMR (CDCl$_3$) δ 7.32 (d, 1H); 6.73 (d, 1H); 6.59 (dd, 1H); 5.63 (s, 1H).

(3b)
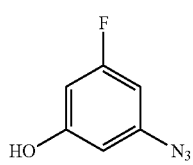

(3c)
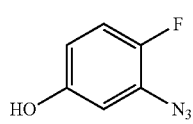

(3d)
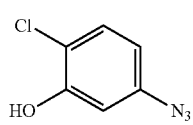

3-azido-2-fluorophenol (3e). 40% yield. $^1$H NMR (CDCl$_3$) δ 6.99 (m, 1H); 6.80 (m, 1H); 6.67 (m, 1H); 5.25 (s, 1H).

5-azido-2-bromophenol (3f). 31% yield. $^1$H NMR (CDCl$_3$) δ 7.43 (d, 1H); 6.73 (d, 1H); 6.54 (dd, 1H); 5.60 (s, 1H).

3-azido-2-chlorophenol (3g). 60% yield. $^1$H NMR (CDCl$_3$) δ 7.22 (t, 1H); 6.84 (dd, 1H); 6.80 (dd, 1H); 5.70 (s, 1H).

5-azido-2-methylphenol (3h). 29% yield. $^1$H NMR (CDCl$_3$) δ 7.09 (d, 1H); 6.56 (dd, 1H); 6.49 (d, 1H); 5.36 (s, 1H); 2.23 (s, 3H).

(3e)
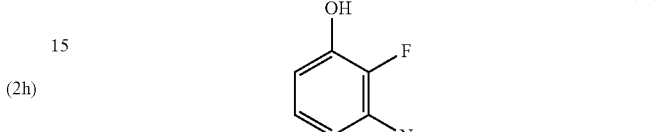

(3f)
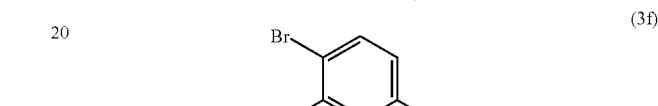

(3g)
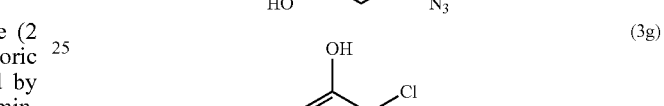

(3h)
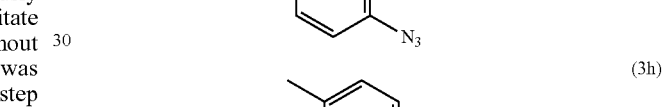

3-azido-2-methylphenol (3i). 20% yield. $^1$H NMR (CDCl$_3$) δ 7.12 (t, 1H); 6.77 (d, 1H); 6.60 (d, 1H); 4.78 (s, 1H); 2.13 (s, 3H).

3-azido-5-chlorophenol (3j). 72% yield. $^1$H NMR (CDCl$_3$) δ 6.65 (d, 2H); 6.42 (t, 1H); 5.10 (s, 1H).

3-azido-5-(trifluoromethyl)phenol (3k). 15% yield. $^1$H NMR (d$_6$-DMSO) δ 10.52 (s, 1H); 6.87 (s, 1H); 6.84 (s, 1H); 6.77 (s, 1H).

3-azido-2,6-difluorophenol (3l). 13% yield. $^1$H NMR (CDCl$_3$) δ 6.91 (m, 1H); 6.60 (m, 1H); 5.56 (s, 1H).

3-azido-2-chloro-6-methylphenol (3m). 86% yield. $^1$H NMR (CDCl$_3$) δ 7.06 (d, 1H); 6.70 (d, 1H); 5.77 (s, 1H); 2.28 (d, 3H).

(3i)
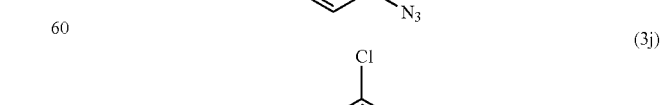

(3j)
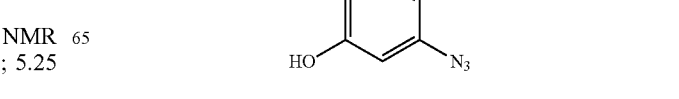

-continued

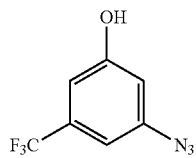
(3k)

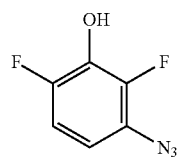
(3l)

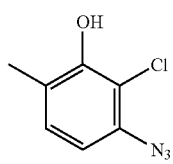
(3m)

N-(5-chloro-2-methylphenyl)propiolamide

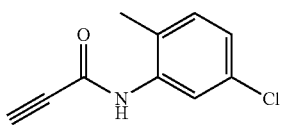

Propiolic acid (7 g, 0.1 mol) was dissolved in acetonitrile (400 mL) then cooled to 0° C. DCC (22.7 g, 0.11 mol) was added, followed by 4 (21.24 g, 0.15 mol), then the reaction was stirred to RT over 18 hr. The precipitated DCU was removed by filtration, then the clear solution was concentrated. The crude solid was washed with hexanes, followed by DCM. Additional product was precipitated from the DCM fraction at 0° C. The product was combined and dried to give 12.57 g of 5 (65% yield). $^1$H NMR (CDCl$_3$) δ 7.99 (s, 1H); 7.12 (q, 2H); 2.99 (s, 1H); 2.29 (s, 3H).

General procedure for triazole coupling. Starting azide (3a-i) (1 mmol), 5 (0.19 g, 1 mmol), CuSO$_4$·5H$_2$O (25 mg, 0.1 mmol), and sodium ascorbate (0.1 g, 0.5 mmol) were dissolved in 5 mL of EtOH. The reaction was refluxed for 18 hr at 80° C. After cooling to RT the reaction mixture was diluted with 10 mL of 50% EtOH/50% H$_2$O, then the resulting precipitate was collected by filtration.

N-(5-chloro-2-methylphenyl)-1-(4-fluoro-3-hydroxyphenyl)-1H-1,2,3-triazole-4-carboxamide (TR001)

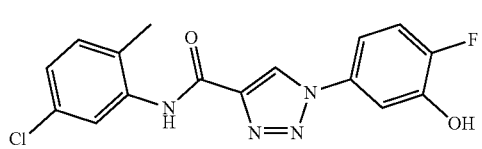 [SMILES: Cc1ccc(Cl)cc1NC(=O)c1cn(-c2ccc(F)c(O)c2)nn1]

76% yield. $^1$H NMR (d$_6$-DMSO) δ 10.10 (s, 1H); 9.37 (s, 1H); 7.62 (d, 1H); 7.58 (d, 1H); 7.41 (d, 2H); 7.32 (d, 1H); 7.24 (dd, 1H); 2.77 (s, 3H).

N-(5-chloro-2-methylphenyl)-1-(3-fluoro-5-hydroxyphenyl)-1H-1,2,3-triazole-4-carboxamide (TR002)

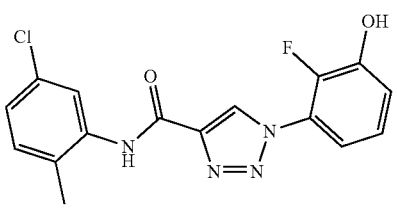 [SMILES: Cc1ccc(Cl)cc1NC(=O)c1cn(-c2cccc(O)c2F)nn1]

30% yield. $^1$H NMR (d$_6$-DMSO) δ 10.65 (s, 1H); 10.17 (s, 1H); 9.47 (s, 1H); 7.61 (s, 1H); 7.39 (d, 1H); 7.32 (m, 2H); 7.24 (t, 1H); 6.75 (d, 1H); 2.74 (s, 3H).

N-(5-chloro-2-methylphenyl)-1-(2-fluoro-3-hydroxyphenyl)-1H-1,2,3-triazole-4-carboxamide (TR003)

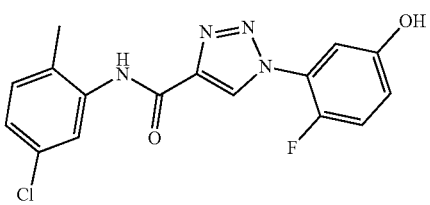 [SMILES: Cc1ccc(Cl)cc1NC(=O)c1cn(-c2cc(O)ccc2F)nn1]

62% yield. $^1$H NMR (d$_6$-DMSO) δ 10.68 (s, 1H); 10.18 (s, 1H); 9.19 (s, 1H); 7.61 (s, 1H); 7.33 (t, 1H); 7.24 (m, 4H), 2.28 (s, 3H).

N-(5-chloro-2-methylphenyl)-1-(2-fluoro-5-hydroxyphenyl)-1H-1,2,3-triazole-4-carboxamide (TR004)

71% yield. $^1$H NMR (d$_6$-DMSO) δ 10.18 (s, 1H); 10.13 (s, 1H); 9.17 (d, 1H); 7.60 (s, 1H); 7.44 (t, 1H); 7.36 (d, 1H); 7.23 (m, 2H); 7.00 (m, 1H); 2.27 (s, 3H).

N-(5-chloro-2-methylphenyl)-1-(2,4-difluoro-3-hydroxyphenyl)-1H-1,2,3-triazole-4-carboxamide) (TR005)

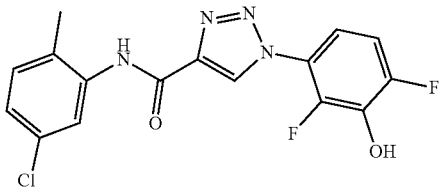 [SMILES: Cc1ccc(Cl)cc1NC(=O)c1cn(-c2ccc(F)c(O)c2F)nn1]

61% yield. $^1$H NMR (d$_6$-DMSO) δ 11.13 (s, 1H); 10.20 (s, 1H); 9.19 (s, 1H); 7.60 (s, 1H); 7.30 (d, 3H); 2.28 (s, 3H).

N-(5-chloro-2-methylphenyl)-1-(4-chloro-3-hydroxyphenyl)-1H-1,2,3-triazole-4-carboxamide (TR006)

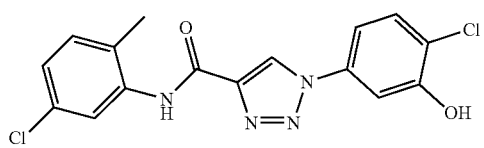 [SMILES: Cc1ccc(Cl)cc1NC(=O)c1cn(-c2ccc(Cl)c(O)c2)nn1]

96% yield. $^1$H NMR (d$_6$-DMSO) δ 10.12 (s, 1H); 9.41 (s, 1H); 7.26 (s, 3H); 7.44 (s, 1H); 7.32 (d, 1H); 7.24 (d, 1H); 2.51 (s, 3H).

N-(5-chloro-2-methylphenyl)-1-(2-chloro-3-hydroxyphenyl)-1H-1,2,3-triazole-4-carboxamide (TR007)

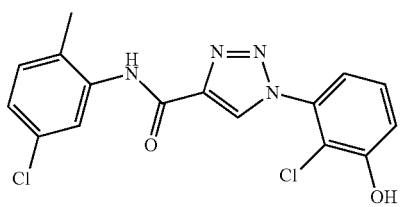 [SMILES: Cc1ccc(Cl)cc1NC(=O)c1cn(-c2cccc(O)c2Cl)nn1]

85% yield. $^1$H NMR (d$_6$-DMSO) δ 11.01 (s, 1H); 10.18 (s, 1H); 9.17 (s, 1H); 7.62 (s, 1H); 7.39 (m, 1H); 7.32 (m, 1H); 7.24 (m, 2H); 7.18 (m, 1H); 2.28 (s, 3H).

N-(5-chloro-2-methylphenyl)-1-(3-chloro-5-hydroxyphenyl)-1H-1,2,3-triazole-4-carboxamide (TR008)

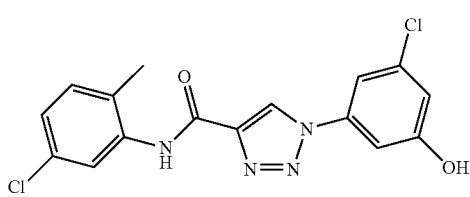 [SMILES: Cc1ccc(Cl)cc1NC(=O)c1cn(-c2cc(O)cc(Cl)c2)nn1]

82% yield. $^1$H NMR (d$_6$-DMSO) δ 10.65 (s, 1H); 10.16 (s, 1H); 9.48 (s, 1H); 7.60 (d, 2H); 7.42 (s, 1H); 7.32 (d, 1H); 7.24 (d, 1H); 6.98 (s, 1H); 2.27 (s, 3H).

1-(4-bromo-3-hydroxyphenyl)-N-(5-chloro-2-methylphenyl)-1H-1,2,3-triazole-4-carboxamide (TR009)

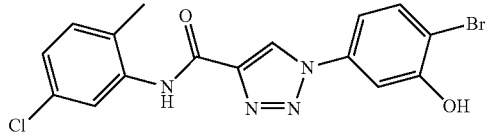 [SMILES: Cc1ccc(Cl)cc1NC(=O)c1cn(-c2ccc(Br)c(O)c2)nn1]

81% yield. $^1$H NMR (d$_6$-DMSO) δ 11.03 (s, 1H); 10.16 (s, 1H); 9.43 (s, 1H); 7.74 (d, 1H); 7.60 (m, 2H); 7.38 (d, 1H); 7.32 (d, 1H); 7.24 (m, 1H); 2.27 (s, 3H).

N-(5-chloro-2-methylphenyl)-1-(2-chloro-3-hydroxy-4-methylphenyl)-1H-1,2,3-triazole-4-carboxamide (TR010)

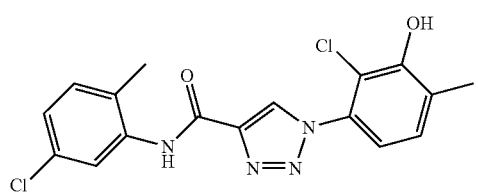 [SMILES: Cc1ccc(Cl)cc1NC(=O)c1cn(-c2ccc(C)c(O)c2Cl)nn1]

90% yield. $^1$H NMR (d$_6$-DMSO) δ 10.14 (s, 1H); 9.90 (s, 1H); 9.12 (s, 1H); 7.62 (d, 1H); 7.32 (d, 2H); 7.24 (dd, 1H); 7.14 (d, 1H); 2.32 (s, 3H); 2.28 (s, 3H).

N-(5-chloro-2-methylphenyl)-1-(3-hydroxy-4-methylphenyl)-1H-1,2,3-triazole-4-carboxamide (TR011)

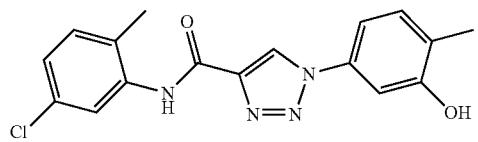 [SMILES: Cc1ccc(-n2cc(C(=O)Nc3cc(Cl)ccc3C)nn2)cc1O]

65% yield. $^1$H NMR (d$_6$-DMSO) δ 10.11 (s, 1H); 10.05 (s, 1H); 9.34 (s, 1H); 7.62 (s, 1H); 7.41 (s, 1H); 7.31 (m, 3H); 7.23 (d, 1H); 2.27 (s, 3H); 2.19 (s, 3H).

N-(5-chloro-2-methylphenyl)-1-(3-hydroxy-2-methylphenyl)-1H-1,2,3-triazole-4-carboxamide (TR012)

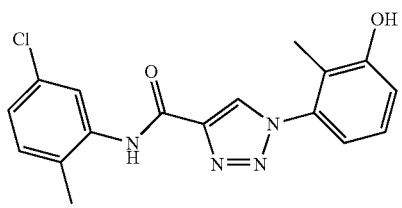 [SMILES: Cc1ccc(Cl)cc1NC(=O)c1cn(-c2cccc(O)c2C)nn1]

85% yield. $^1$H NMR (d$_6$-DMSO) δ 10.12 (s, 1H); 10.10 (s, 1H); 9.07 (s, 1H); 7.63 (d, 1H); 7.32 (d, 1H); 7.24 (m, 2H); 7.05 (d, 1H); 6.95 (d, 1H); 2.28 (s, 3H); 1.93 (s, 3H).

N-(5-chloro-2-methylphenyl)-1-(3-(trifluoromethyl)-5-hydroxyphenyl)-1H-1,2,3-triazole-4-carboxamide (TR013)

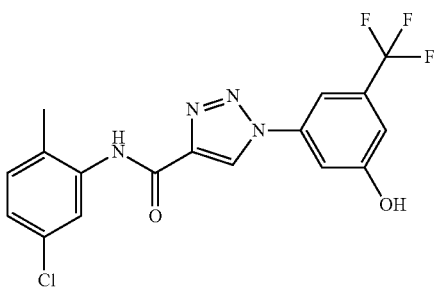 [SMILES: Cc1ccc(Cl)cc1NC(=O)c1cn(-c2cc(O)cc(C(F)(F)F)c2)nn1]

32% yield. $^1$H NMR (d$_6$-DMSO) δ 10.89 (s, 1H); 10.19 (s, 1H); 9.60 (s, 1H); 7.84 (s, 1H); 7.73 (s, 1H); 7.61 (s, 1H); 7.33 (d, 1H); 7.24 (m, 2H); 2.28 (s, 3H).

Biological Evaluation, In Vitro Studies

Reagents. General reagents were from Sigma-Aldrich or Fisher. CsA, phenylarsine oxide, diamide, N-ethylmaleimide, carbonyl cyanide-4-(trifluoromethoxy)phenylhydrazone (FCCP) were from Sigma-Aldrich, digitonin was from Acros organics, rhodamine 123 (Rh123) and Calcium Green-5N were from ThermoFisher Scientific, copper-o-phenanthroline was prepared just before use by mixing CuSO$_4$ with o-phenanthroline at a 1:2 molar ratio in double-distilled water.

Plasma stability determination. The degradation of TR001 in the presence of mouse plasma (from Innovative Research) was used to predict the plasma stability of the compound to esterase catalyzed hydrolysis. A positive control for plasma cholinesterase, propantheline bromide, was included in all assays. Briefly, murine plasma was incubated with 1 μm TR001. Aliquots were removed at t=0, 5, 15, 30, and 60 and 120 min and quenched with acetonitrile containing structurally related compound (TR073) as the internal standard. The amount of TR001 remaining in the supernatant was assessed by LC-MS/MS in multiple reaction monitoring mode (MRM) using a 4000 QTRAP (SCIEX) with electrospray ionization source. The instrument was operated in negative mode with source parameters: source voltage ~4500 kV, GS1 50, GS2 50, CUR 30, TEM 650 and CAD gas MED. Optimal MRM transitions were obtained by direct infusion of the pure compound into the source. The mass spectrometer was interfaced to a Shimadzu (Columbia, MD) SIL-20AC XR auto-sampler maintained at 35° C. followed by 2 LC-20AD XR LC pumps. The internal standard and compound of interest were resolved using a Gemini-NX C18 50×2.1 mm column (Phenomenex) with 0.1% formic acid (solvent A) and 0.1% formic acid in acetonitrile (solvent B). The injection volume was 10 μL at a flow rate of 0.75 mL/min. The gradient elution was 10% B to 95% B over 5 min and held at 95% for 1 min before returning to start conditions. The column was maintained at 40° C. using a Shimadzu CTO-20AC column oven. Data were acquired using Analyst 1.6.2 and analyzed using Multiquant 3.0.1 software. The first-order rate constant for substrate depletion was determined from a linear least squares fit of the natural log of the percent parent compound remaining versus time. The rate constant was used to calculate the plasma half-life as an indicator of stability.

Mouse studies. All procedures were approved by the Institutional Animal Care and Use Committee (IACUC) at Oregon Health and Science University (IP00000689 to M.F.).

Isolation of mitochondria. C57BL6/N mouse liver mitochondria were prepared from 2 to 6 month old male mice by standard differential centrifugation. Mice fed ad libitum were euthanized with CO$_2$ followed cervical dislocation, their livers were existed and placed in a glass beaker containing ice-cold isolation buffer (IB: 0.25 m sucrose, 10 mm Tris-HCl, 0.1 mm EGTA-Tris, pH 7.4) supplemented with fatty acid free bovine serum albumin. Livers were then cut into small pieces with scissors, rinsed with ice-cold IB, and passed through a pre-chilled Potter homogenizer with Teflon pestle. The homogenate (~30 mL per liver) was transferred to centrifuge tubes, and unbroken cells and nuclei were removed by centrifugation at 700 g for 10 min at 4° C. The supernatant containing mitochondria and other organelles was transferred to new tubes and centrifuged at 6000 g for 10 min at 4° C. The resulting supernatant was discarded and mitochondrial pellet was carefully suspended in ice-cold IB and spun at 9500 g for 5 min at 4° C. The pellet was suspended in IB to give a protein concentration of ~60-80 mg/mL and stored on ice. Experiments were started immediately and completed within 5 h. Protein concentration was determined by the Biuret method.

Assessment of mitochondrial swelling. Changes in mitochondrial volume of isolated mouse liver mitochondria were followed in a 96-well clear assay plate at a final volume of 0.2 mL and 0.25 mg/mL mitochondrial protein. Absorbance was read for 30 min at 540 nm on a Tecan Infinite F200 plate reader. Activity of test compounds was addressed as follows: First, 0.1 mL of sucrose assay buffer (SAB: 0.250 m sucrose, 10 mm MOPS-Tris, 0.01 mm EGTA-Tris, 1.0 mm phosphoric acid-Tris, 10 mm glutamate and 5 mm malate, pH 7.4) supplemented with twice the CaCl$_2$ concentration required to induce mitochondrial swelling (which was determined for each preparation of mitochondria, typically 50 μm) was dispensed to the assay plate. A set of wells also contained 2.0 mm EGTA (to prevent mitochondrial swelling). The test wells contained a range of concentrations (in 1:2 serial dilutions) of the compounds of interest or 2% DMSO. Experiments were started by the addition of 0.1 mL of mitochondrial suspension (0.5 mg/mL mitochondria in SAB without respiratory substrates) to the assay plates. EC$_{50}$s±SE were determined with OriginPro software by applying Hill1 function fitting algorithm on average concentration response data of n=3-41 independent preparations.

Assessment of mitochondrial membrane potential. Mitochondrial membrane potential—to evaluate toxicity—of isolated mouse liver mitochondria was assessed based on fluorescence quenching of the cationic fluorescent dye Rh123 upon its accumulation into mitochondrial matrix due to inside negative membrane potential. Compounds that interfere with the build-up or maintenance of IMM potential would shift Rh123 fluorescence to higher values compared to DMSO treated samples. Uncoupler FCCP was used to account for nonspecific fluorescence. First, 0.1 mL of SAB was dispensed to a 96-well black assay plate. A set of wells also contained 0.8 μm FCCP (to prevent Rh123 uptake). The test wells contained a range of concentrations (in 1:2 serial dilutions) of the compounds of interest or 2% DMSO. Then, 0.1 mL of 0.5 mg/mL mitochondria in SAB devoid of respiratory substrates but supplemented with 0.8 μm Rh123 were added to all wells of the assay plate. Fluorescence intensity (ex/em 485/535 nm) was read on a Tecan Infinite F200 plate reader for 7 min and value at 5 min was considered for analysis. $EC_{50}s \pm SE$ were determined with OriginPro software by applying Hill1 function fitting algorithm on average concentration response data of n=3 independent preparations.

Assessment of $Ca^{2+}$ retention capacity (CRC). CRC of isolated mouse liver mitochondria was assessed as follows: First, 0.1 mL of SAB were dispensed to a 96-well black assay plate in the presence of 2% DMSO (control wells) or varying concentrations of test compounds, in 1:2 serial dilutions. Then, 0.1 mL of 0.5 mg/mL mitochondria in SAB devoid of respiratory substrates, but supplemented with 1 μm Calcium Green-5N were added to all wells of the assay plate. A train of 10 μm $CaCl_2$ pulses was added at 2 min intervals, and fluorescence intensity (ex/em 485/535 nm) was read on Tecan Infinite F200 plate reader.

Cell culture. HeLa and Hek239T cells were grown in Dulbecco's modified Eagle's medium (DMEM) supplemented with 10% fetal bovine serum, 100 U/mL penicillin and 100 mg/mL streptomycin in a humidified atmosphere of 5% $CO_2$/95% air at 37° C.

Generation of CyPD-null cells. The CRISPR/Cas9 system was used to create HEK293T lines lacking the expression of the gene, Ppif, encoding CyPD. The guide used for the CRISPR was CCGACCCGCGCCCGCGATGC (TGG) (SEQ ID NO: 1), which targets the second amino acid of the coding sequence. Following transfection, individual cell lines were selected and expanded as outlined in Antoniel et al. [26]. Western blot analysis of selected clones indicated the absence of CyPD protein in several clones. Subsequent sequence analysis of these null clones indicated the introduction of an early frame shift mutation that halted protein expression.

CRC of permeabilized cells. Wild-type or CyPD-null HEK239T cells were cultured for 48 h to reach 70-80% confluency, then harvested by trypsinization and washed in KCl buffer (KB: 0.13 m KCl, 10 mm MOPS-Tris, 1 mm phosphoric acid-Tris, 0.1 mm EGTA-Tris, pH 7.4). Cells were then suspended in KB (except that EGTA-Tris was increased to 1.0 mm) to $10^6$ cells/mL and treated with 0.1 mm digitonin for 10 min on ice to permeabilize the plasma membrane. Following excess digitonin elimination by washing cells twice in ice-cold KB, the cells were suspended to $2 \times 10^7$ cells per mL in ice-cold KB containing 10 μm EGTA-Tris and kept on ice. CRC was assessed in a black 96-well plate in a final volume of 0.2 mL and buffer containing 0.13 m KCl, 10 mm MOPS-Tris, 1 mm phosphoric acid-Tris, 0.01 mm EGTA-Tris, 5 mm glutamate, 2.5 mm malate and 0.5 μm Calcium Green-5N. A train of 10 μm $Ca^{2+}$ pulses was added at 4 min intervals, and fluorescence intensity (ex/em 485/535 nm) was read on Tecan Infinite F200 plate reader.

Measurement of respiration. Mitochondrial oxygen consumption of isolated mitochondria or HeLa cell monolayer was assessed with the Seahorse Extracellular Flux Analyzer XF24 (Seahorse Bioscience, Billerica, MA, USA). Isolated mouse liver mitochondria: Mitochondrial assay solution contained 220 mm mannitol, 70 mm sucrose, 25 mm MOPS-Tris, 10 mm Pi-Tris, 5 mm $MgCl_2$, 1 mm EGTA-Tris, 0.2% fatty acid free BSA, 5 mm succinate and 2 μm rotenone, pH 7.4. Mitochondria (5 μg, suspended in 50 μL mitochondrial assay solution) were added to each well of an XF24 cell culture microplate, centrifuged at 2000 g for 20 min at 4° C. and then supplemented with 450 μL of mitochondrial assay solution containing 4 mm ADP to initiate the experiments. Additions were as indicated in FIG. 5A.

HeLa cells: cells were seeded at a density of $3 \times 10^4$ per well in 0.2 mL DMEM and cultured for 24 h. Assays were started by re-placing the growth medium with 0.5 mL serum and antibiotic-free unbuffered DMEM (pH 7.4) and additions were made as indicated in FIG. 5C.

Cell viability assay. HeLa cells were seeded at a density of $10^4$ per well in 96-well plates and let to adhere for 6 h before treatment with varying concentrations of TR001 or vehicle (1% DMSO. After treatment for 24 h the relative viable cell number was determined with a CellTiter 96 Aqueous One Solution Cell Proliferation Assay Kit (Promega).

Biological Evaluation, In Vivo Studies in Zebrafish

Zebrafish studies. Wildtype adult zebrafish were maintained in the Zebrafish Facility of the Biology Department of the University of Padova in aerated saline water, which was continuously filtered by a circulating system, at 28.5° C. with a precise light/dark cyclic conditions (14/10 hours), according to standard protocols [27,28]. To obtain embryos for injection experiments, two or three females were paired with two or three males in a 1.5 litre tank and separated by a transparent wall until morning. The next morning, the transparent wall was removed and the zebrafish were free for courtship and mating. Fertilized eggs were collected and kept in fish water, containing 0.5 mm $NaH_2PO_4$ (Sigma-Aldrich, S8282), 0.5 mm $NaHPO_4$ (Sigma-Aldrich, S7909) and 3 mg/L instant ocean (Instant Ocean, SS15-10), at 28.5° C. All procedures were approved by the OPBA of the University of Padova and authorized by the Italian Ministry of Health (415/2015).

Morpholino antisense injection and treatment. Knockdown of col6a1 gene expression was obtained with a previously published morpholino [25] with sequence GAG AGC GGA AGA CGA ACC TTC ATT C (SEQ ID NO: 2; GeneTools, Inc.). A control morpholino with no sequence homology in the zebrafish genome was used in parallel (CCT CTT ACC TCA GTT ACA ATT TAT A; SEQ ID NO: 3). Zebrafish eggs from wild-type matings were injected at the 1-2 cell stage with approximately 10 nL of 0.1 mm morpholino solution (corresponding to 4 ng of morpholino) using a WPI pneumatic PicoPump PV820 injector (World Precision Instruments, Inc.). Zebrafish embryos were dechorionated at 20 hours post fertilization (hpf) and treated at 21 hpf with increasing doses (0.1, 1 and 10 μm) of both TR001 and 63 compounds dissolved in fish water with 1% DMSO (vehicle).

Motor activity. The number of spontaneous coiling events performed in 15 seconds by single zebrafish embryos was recorded at 24 hpf by light microscopy. Touch-evoked escape responses were recorded at 48 hpf by observing the ability of zebrafish embryos to escape after a tail-touch with a little tip. Embryos were subdivided in 4 groups according to the observed phenotype: paralyzed embryos, score 0; underdeveloped embryos showing only coiling events, score 1; embryos showing lower motility, score 2; normal embryos, score 3.

Survival. Zebrafish survival was monitored every 3 days for 30 days. Drug treatment with both TR001 and 63 dissolved in fish water with 1% DMSO started at 21 hpf. After 3 days of treatment (4 days post fertilization, dpf), zebrafish were moved to a bigger tank (50 mL) with fresh compounds dissolved in 1% DMSO. As a control vehicle, fish water with 1% DMSO was used.

Birefringence. Muscle structure was monitored by birefringence analysis, taking advantage of muscle anisotropy, which is the ability of muscle fibers to refract polarized light. Briefly, zebrafish embryos at 48 hpf were anesthetized with 0.02% Tricaine (Sigma-Aldrich, E10521) and placed in 2% methylcellulose (Sigma-Aldrich, M0387) on a rectangular glass plate, which was positioned on the light path of a Leica M165FC stereomicroscope (Leica, Inc.). Two polarized filters were used, the first placed between the light source and the glass slide, light being refracted through muscle fibers; the second was placed above the zebrafish embryos and rotated at a 90° angle relative to the first filter. With this set-up, light refracted by muscle fibers (due to the pseudo-crystalline array of sarcomeres) is transmitted and analyzed. Integrated area of birefringence was calculated using ImageJ software. Birefringence values $3\times10^6$ pixels are typical of wild-type embryos, while values between 1 and $3\times10^6$ pixels and values s $1\times10^6$ pixels were taken to indicate a mild and severe myopathy, respectively [25,29].

OCR measurement. The Seahorse XF-24 extracellular flux analyzer (Agilent Technologies, United States, California, Santa Clara) was used to measure oxygen consumption rate in col6a1 zebrafish morphants at 48 hpf. One day prior to analysis, each well of the Seahorse XF-24 extracellular flux analyzer cartridge (Agilent Technologies, 101122-100) was filled with 1 mL of Seahorse XF Calibrant (Agilent Technologies, 100840-000) and placed at 37° C. overnight. The day after, zebrafish embryos at 48 hpf were placed in a XF-24 islet capture microplate (one zebrafish per well). Each well was filled with 670 μL of fish water and an islet capture screen was fixed on top of each well to prevent zebrafish from moving out of the measurement chamber. Subsequently, after calibration of the Seahorse XF 24 Extracellular Flux Analyzer cartridge, the XF-24 capture microplate was loaded in the Seahorse XF-24 Extracellular Flux Analyzer. First, basal respiration was measured. Second, respiration due to ATP synthase was measured after addition of 10 μm oligomycin (Merck Millipore-495455). Third, maximal respiration capacity was measured by adding 2 μm of the uncoupler carbonyl cyanide-4-(trifluoromethoxy)phenylhydrazone (FCCP, Sigma-Aldrich, C2920). Last, 1 μm of the complex I inhibitor, rotenone (Sigma-Aldrich, R8875), and 1 μm of the complex III inhibitor, antimycin A (Sigma-Aldrich, A8674) were added to determine non-mitochondrial (residual) respiration.

COMPARATIVE EXAMPLES

| Structure | Mouse Liver Mitochondria (MLM) | | |
|---|---|---|---|
| | $CRC/CRC_0$ at 1.25 μM | Swelling $EC_{50}$ (nM) | Rh123 $EC_{50}$ (μM) |
| CSA | 3.6 | 200 | >100 |
| (isoxazole compound) | 13.5 | 2 | >100 |
| (triazole compound) | 7.4 | 25 | >100 |

-continued

| Structure | Mouse Liver Mitochondria (MLM) | | |
|---|---|---|---|
| | CRC/CRC$_0$ at 1.25 μM | Swelling EC$_{50}$ (nM) | Rh123 EC$_{50}$ (μM) |
| triazole carboxamide with 4-F, 3-OH phenyl | 1 | 4 μM | 10 |
| triazole carboxamide with benzimidazolone | 1 | >20 μM | — |
| triazole carboxamide with 4-F, 3-NHAc phenyl | 1 | >20 μM | — |
| triazole carboxamide with 4-F, 3-NHC(O)CF$_3$ phenyl | 1 | >20 μM | — |
| triazole carboxamide with 2-F, 3-OH phenyl | 7.8 | 152 | 29 |
| triazole carboxamide with 3-OH, 5-F phenyl | 13.09 | 10 | 14 |
| triazole carboxamide with 2-F, 5-OH phenyl | 1.4 | >20 μM | >40 |
| triazole carboxamide with 4-F, 3-OAc phenyl | 4.5 | 83 | >40 |

| Structure | Mouse Liver Mitochondria (MLM) | | |
|---|---|---|---|
| | CRC/CRC$_0$ at 1.25 μM | Swelling EC$_{50}$ (nM) | Rh123 EC$_{50}$ (μM) |
| | 1.8 | 581 | >40 |
| | 1.8 | 8.7 μM | >40 |
| 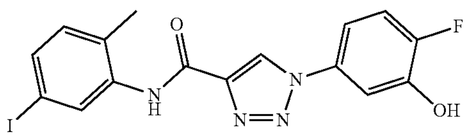 [SMILES: Cc1ccc(I)cc1NC(=O)c1cn(-c2ccc(F)c(O)c2)nn1] | 8.3 | 28 | 14.7 |
| 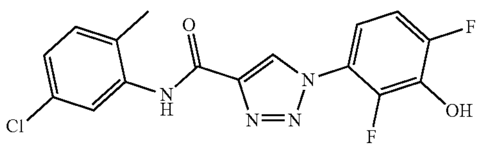 [SMILES: Cc1ccc(Cl)cc1NC(=O)c1cn(-c2ccc(F)c(O)c2F)nn1] | 2.6 | 782 | >40 |
| 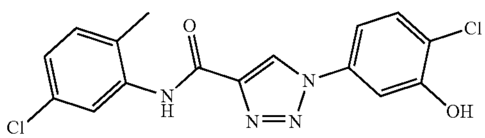 [SMILES: Cc1ccc(Cl)cc1NC(=O)c1cn(-c2ccc(Cl)c(O)c2)nn1] | 3.9 | 135 | >40 |
| 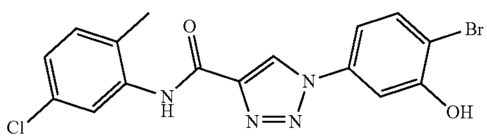 [SMILES: Cc1ccc(Cl)cc1NC(=O)c1cn(-c2ccc(Br)c(O)c2)nn1] | 2.4 | 475 | >40 |
| | 1 | >20 μM | — |
| | 1 | >20 μM | — |
| | 1 | >20 μM | — |
| | 1 | >20 μM | — |

-continued
| Structure | CRC/CRC$_0$ at 1.25 μM | Swelling EC$_{50}$ (nM) | Rh123 EC$_{50}$ (μM) |
|---|---|---|---|
| 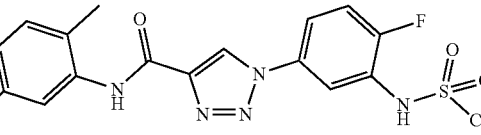 | 1 | >20 μM | — |
| 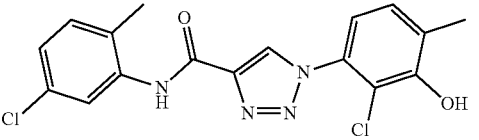 [SMILES: Cc1ccc(Cl)cc1NC(=O)c1cn(-c2ccc(C)c(O)c2Cl)nn1] | 1 | >20 μM | >40 |
| 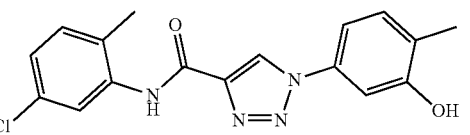 | 1.4 | >20 μM | >40 |
| 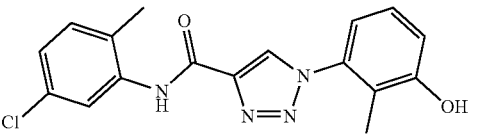 [SMILES: Cc1ccc(Cl)cc1NC(=O)c1cn(-c2cccc(O)c2C)nn1] | 1.4 | 10.6 μM | >40 |
| 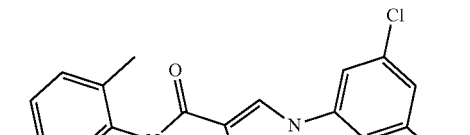 | 7.3 | 28 | >40 |
| 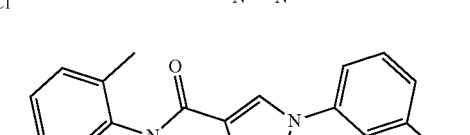 | 1.2 | >20 μM | >40 |
| 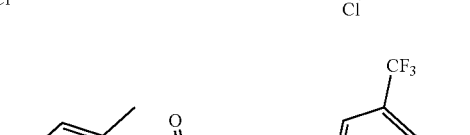 | 3 | 534 | 6 |
| 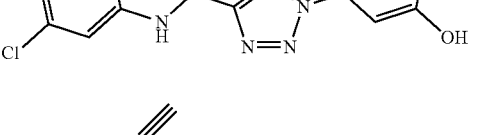 | 3.7 (MC001 = 6.2) | 513 | >40 |

| Structure | Mouse Liver Mitochondria (MLM) | | |
|---|---|---|---|
| | CRC/CRC$_0$ at 1.25 μM | Swelling EC$_{50}$ (nM) | Rh123 EC$_{50}$ (μM) |
| (structure) | | >20 μM | |
| (structure) | 3.9 (MC001 = 5.6) | 153 | — |
| (structure) | | | |
| (structure) | | | |
| (structure) | 1.5 | >20 μM | — |
| (structure) | 5.4 (MC001 = 6.2) | 5.1 (MC001 = 19) | >40 |
| (structure) | 2.4 (MC001 = 6.2) | 578 | >40 |
| (structure) | 1.3 (MC001 = 6.2) | 7 μM | >40 |

-continued

| Structure | Mouse Liver Mitochondria (MLM) | | |
|---|---|---|---|
| | $CRC/CRC_0$ at 1.25 µM | Swelling $EC_{50}$ (nM) | Rh123 $EC_{50}$ (µM) |
| (structure shown) | 1.4 (MC001 = 6.2) | 5.2 µM | >40 |

Methods of Treatment

The compounds described herein are useful in the diagnosis and treatment of a variety of human diseases including neurodegenerative and neurological disorders, consequences of stroke and/or cerebral ischemia, hypoxia, multi-infarct dementia, consequences of trauma and damages to the cerebrum or spinal cord, autoimmune disease, and psychiatric illness. For example, the compounds described herein are particularly useful in treating neurodegenerative disorders such as Huntington's disease and other polyglutamine disorders, ischemic reperfusion injury, multiple sclerosis, amyotrophic lateral sclerosis, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis, diabetic retinopathy, muscular dystrophy, traumatic brain injury, type II diabetes, heart infarction, stroke, high-pressure neurological syndrome, dystonia, olivopontocerebellar atrophy, frontotemporal dementia, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasites, for example, poliomyelitis, Lyme disease (*Borrelia burgdorferi* infection) and malaria, cancers with cerebral localization, Tourette's syndrome, hepatic encephalopathy, systemic lupus, analgesia and opiate withdrawal symptoms, feeding behavior, schizophrenia, chronic anxiety, depressive disorders, disorders of the developing or aged brain, diseases of addiction, all peripheral indications such as diabetes, and complications thereof.

Provided is a method of treatment for each of the diseases and conditions above. Each method comprises administering to a subject in need thereof a pharmaceutically effective amount of a compound described herein, or a pharmaceutically acceptable salt thereof.

For instance, provided is a method of treatment for Alzheimer's disease in a human subject, the method comprising administering to the human in need thereof a pharmaceutically effective amount of a compound of Formula (I), or a pharmaceutically acceptable salt thereof:

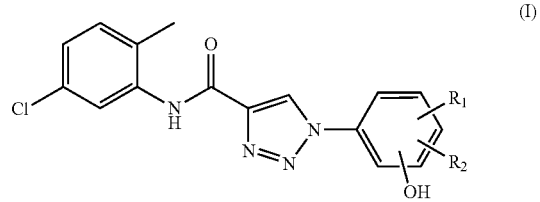

(I)

wherein $R_1$ is selected from the group of H, halogen, and $C_1$-$C_3$ alkyl;

and $R_2$ is selected from the group of H, $CF_3$, and halogen;

with the proviso that at least one of $R_1$ and $R_2$ is halogen or $CF_3$.

Also provided is a use of a compound of Formula (I), or a pharmaceutically acceptable salt thereof, as defined above, in the preparation of a medicament for the treatment of each of the diseases or conditions above. For instance, provided is the use of a compound of Formula (I), or a pharmaceutically acceptable salt thereof:

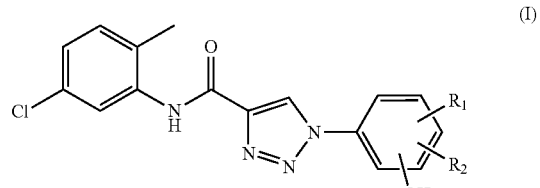

(I)

wherein $R_1$ is selected from the group of H, halogen, and $C_1$-$C_3$ alkyl; and $R_2$ is selected from the group of H, $CF_3$, and halogen; with the proviso that at least one of $R_1$ and $R_2$ is halogen or $CF_3$; in the preparation of a medicament for use in the treatment of Alzheimer's disease in a human subject.

It is understood that such uses in the preparation of a medicament apply to the compounds of Formula (II).

Pharmaceutical Compositions

Also provided herein is a pharmaceutical composition comprising a pharmaceutically effective amount of a compound of Formula (I), or a pharmaceutically acceptable salt thereof:

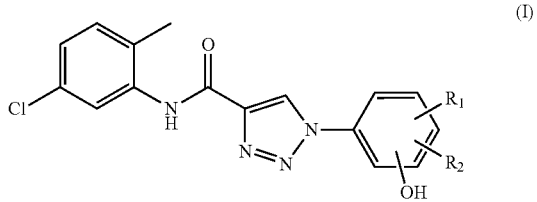 (I)

wherein $R_1$ is selected from the group of H, halogen, and $C_1$-$C_3$ alkyl; and $R_2$ is selected from the group of H, $CF_3$, and halogen; with the proviso that at least one of $R_1$ and $R_2$ is halogen or $CF_3$; and a pharmaceutically acceptable carrier or excipient.

A composition containing a pharmaceutically effective amount of one or more of the isotopic compounds described herein, or a pharmaceutically acceptable salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in Remington: The Science and Practice of Pharmacy, 21$^{st}$ Ed., Gennaro, Ed., Lippencott Williams & Wilkins (2005) and in The United States Pharmacopeia: The National Formulary (USP 36 NF31), published in 2013.

As used herein, "pharmaceutically acceptable excipient" is a pharmaceutically acceptable vehicle that includes, without limitation, any and all carriers, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "carrier" refers to an excipient or vehicle that includes without limitation diluents, disintegrants, precipitation inhibitors, surfactants, glidants, binders, lubricants, and the like with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

REFERENCES

[1] G. Szabadkai, M. R. Duchen, *Physiology* 2008, 23, 84-94.
[2] T. E. Gunter, S.-S. Sheu, *Biochim. Biophys. Acta—Bioenerg.* 2009, 1787, 1291-1308.
[3] P. Bernardi, A. Krauskopf, E. Basso, V. Petronilli, E. Blalchy-Dyson, F. Di Lisa, M. A. Forte, *FEBS J.* 2006, 273, 2077-2099.
[4] P. Bernardi, M. Forte, *Novartis Found. Symp.* 2007, 287, 157-64; discussion 164-9.
[5] P. Bernardi, *Biochim. Biophys. Acta—Bioenerg.* 1996, 1275, 5-9.
[6] L. Azzolin, S. von Stockum, E. Basso, V. Petronilli, M. A. Forte, P. Bernardi, *FEBS Lett.* 2010, 584, 2504-2509.
[7] P. Bernardi, F. Di Lisa, *J. Mol. Cell. Cardiol.* 2015, 78, 100-106.
[8] J. Šileikytė, E. Blachly-Dyson, R. Sewell, A. Carpi, R. Menabo, F. Di Lisa, F. Ricchelli, P. Bernardi, M. Forte, *J. Biol. Chem.* 2014, 289, 13769-13781.
[9] V. Giorgio, S. von Stockum, M. Antoniel, A. Fabbro, F. Fogolari, M. Forte, G. D. Glick, V. Petronilli, M. Zoratti, I. Szabo, et al., *Proc. Nat. Acad. Sci.* 2013, 110, 5887-5892.
[10] J. Šileikytė, M. Forte, *Oxid. Med. Cell. Longev.* 2019, 2019, 1-11.
[11] E. Basso, L. Fante, J. Fowlkes, V. Petronilli, M. A. Forte, P. Bernardi, *J. Biol. Chem.* 2005, 280, 18558-61.
[12] S. Roy, J. Šileikytė, M. Schiavone, B. Neuenswander, F. Argenton, J. Aubé, M. P. Hedrick, T. D. Y. Chung, M. A. Forte, P. Bernardi, et al., *ChemMedChem* 2015, 10, 1655-1671.
[13] S. Roy, J. Šileikytė, B. Neuenswander, M. P. Hedrick, T. D. Y. Chung, J. Aubé, F. J. Schoenen, M. A. Forte, P. Bernardi, *ChemMedChem* 2016, 11, 283-288.
[14] B. W. Budzik, K. A. Evans, D. D. Wisnoski, J. Jin, R. A. Rivero, G. R. Szewczyk, C. Jayawickreme, D. L. Moncol, H. Yu, *Bioorg. Med. Chem. Lett.* 2010, 20, 1363-1367.
[15] V. D. Filimonov, M. Trusova, P. Postnikov, E. A. Krasnokutskaya, Y. M. Lee, H. Y. Hwang, H. Kim, K.-W. Chi, *Org. Lett.* 2008, 10, 3961-3964.
[16] V. Petronilli, P. Costantini, L. Scorrano, R. Colonna, S. Passamonti, P. Bernardi, *J. Biol. Chem.* 1994, 269, 16638-42.
[17] P. Costantini, R. Colonna, P. Bernardi, *Biochim. Biophys. Acta—Bioenerg.* 1998, 1365, 385-392.
[18] A. Zulian, J. Šileikytė, V. Petronilli, S. Bova, F. Dabbeni-Sala, G. Cargnelli, D. Rennison, M. a Brimble, B. Hopkins, P. Bernardi, et al., *Biochim. Biophys. Acta* 2011, 1807, 1600-5.
[19] A. Zulian, M. Schiavone, V. Giorgio, P. Bernardi, *Pharmacol. Res.* 2016, 113, 563-573.
[20] W. A. Irwin, N. Bergamin, P. Sabatelli, C. Reggiani, A. Megighian, L. Merlini, P. Braghetta, M. Columbaro, D. Volpin, G. M. Bressan, et al., *Nat. Genet.* 2003, 35, 367-371.
[21] E. Palma, T. Tiepolo, A. Angelin, P. Sabatelli, N. M. Maraldi, E. Basso, M. A. Forte, P. Bernardi, P. Bonaldo, *Hum. Mol. Genet.* 2009, 18, 2024-2031.

[22] A. Angelin, T. Tiepolo, P. Sabatelli, P. Grumati, N. Bergamin, C. Golfieri, E. Mattioli, F. Gualandi, A. Ferlini, L. Merlini, et al., *Proc. Natl. Acad. Sci. U.S.A* 2007, 104, 991-6.

[23] T. Tiepolo, a. Angelin, E. Palma, P. Sabatelli, L. Merlini, L. Nicolosi, F. Finetti, P. Braghetta, G. Vuagniaux, J. M. Dumont, et al., *Br. J. Pharmacol.* 2009, 157, 1045-1052.

[24] W. R. Telfer, A. S. Busta, C. G. Bonnemann, E. L. Feldman, J. J. Dowling, *Hum. Mol. Genet.* 2010, 19, 2433-2444.

[25] A. Zulian, E. Rizzo, M. Schiavone, E. Palma, F. Tagliavini, B. Blaauw, L. Merlini, N. M. Maraldi, P. Sabatelli, P. Braghetta, et al., *Hum. Mol. Genet.* 2014, 23, 5353-63.

[26] M. Antoniel, K. Jones, S. Antonucci, B. Spolaore, F. Fogolari, V. Petronilli, V. Giorgio, M. Carraro, F. Di Lisa, M. Forte, et al., *EMBO Rep.* 2018, 19, 257-268.

[27] C. B. Kimmel, W. W. Ballard, S. R. Kimmel, B. Ullmann, T. F. Schilling, *Dev. Dyn.* 1995, 203, 253-310.

[28] A. Avdesh, M. Chen, M. T. Martin-Iverson, A. Mondal, D. Ong, S. Rainey-Smith, K. Taddei, M. Lardelli, D. M. Groth, G. Verdile, et al., *J. Vis. Exp.* 2012, e4196.

[29] M. Schiavone, A. Zulian, S. Menazza, V. Petronilli, F. Argenton, L. Merlini, P. Sabatelli, P. Bernardi, *Pharmacol. Res.* 2017, 125, 122-131.

Definitions

The descriptions herein set forth exemplary methods, parameters and the like. It should be recognized, however, that such description is not intended as a limitation on the scope of the present disclosure but is instead provided as a description of exemplary embodiments.

The terms "pharmaceutically acceptable salt" and "therapeutically acceptable salts" include, for example, salts with inorganic acids and salts with an organic acid. Examples of salts may include hydrochloride, phosphate, diphosphate, hydrobromide, sulfate, sulfinate, nitrate, malate, maleate, fumarate, tartrate, succinate, citrate, acetate, lactate, methanesulfonate (mesylate), benzenesuflonate (besylate), p-toluenesulfonate (tosylate), 2-hydroxyethylsulfonate, benzoate, salicylate, stearate, and alkanoate (such as acetate, HOOC—$(CH_2)_n$—COOH where n is 0-4). In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

Even if not specifically stated in each appearance herein, reference to a compound of Formula (I), and/or a compound of Formula (II), and/or each of the specifically noted compounds, including TR001 through TR013, includes the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds. This applies to all reference to a compound, itself, as well as its use or presence in a pharmaceutical composition, method of treatment, preparation of a medicament, or any other reference herein.

The terms "therapeutically effective amount" or "pharmaceutically effective amount" refer to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I, or a pharmaceutically acceptable salt or co-crystal thereof, is an amount sufficient to inhibit mitochondrial permeability transition pore (mtPTP) activity, and thereby treat a subject (e.g., a human) suffering an indication, or to ameliorate or alleviate the existing symptoms of the indication. For example, a therapeutically or pharmaceutically effective amount may be an amount sufficient to decrease a symptom of a disease or condition responsive to inhibition of mitochondrial permeability transition pore (mtPTP) activity.

The amount of active compound administered will vary depending upon the disease treated, the mammalian species, and the particular mode of administration, etc. Suitable doses for the compounds of the present technology can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

As used herein, the terms "azide," "azido," "$N_3$," "—$N_3$," "$N^-_3$," "—$N^-_3$," "—N=$N^+$=$N^-$," and the moieties:

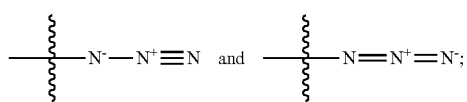

and the like, each refer to a substituent group that is the conjugate base of hydrazoic acid.

The terms "subject" and "patient", and the like, refer to an animal, such as a mammal, that has been or will be the object of treatment, observation or experiment. The methods described herein may be useful in both human therapy and veterinary applications. In some embodiments, the subject is a mammal; in some embodiments the subject is human; and in some embodiments the subject is chosen from cats and dogs. "Subject in need thereof" or "human in need thereof" refers to a subject, such as a human, who may have or is suspected to have diseases or conditions that would benefit from certain treatment; for example treatment with a compound of Formula I, or a pharmaceutically acceptable salt or co-crystal thereof, as described herein. This includes a subject who may be determined to be at risk of or susceptible to such diseases or conditions, such that treatment would prevent the disease or condition from developing.

The terms "halogen" and "halo" refer to F, Cl, Br, or I.

The term, variable, or group referred to as "$C_1$-$C_3$ alkyl" indicates a straight or branched chain alkyl group having 1, 2, or 3 carbon atoms, as represented by methyl, ethyl, n-propyl, and isopropyl groups.

---

---

What is claimed:

1. A compound of Formula (I), or a pharmaceutically acceptable salt thereof:

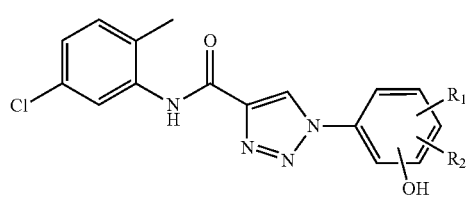

(I)

wherein $R_1$ is selected from the group consisting of H, halogen, and $C_1$-$C_3$ alkyl;

and $R_2$ is selected from the group consisting of H, $CF_3$, and halogen;

with the proviso that at least one of $R_1$ and $R_2$ is halogen or $CF_3$.

2. The compound of claim 1, or a pharmaceutically acceptable salt thereof, wherein $R_1$ is selected from the group consisting of H, F, Cl, Br, and $C_1$-$C_3$ alkyl; and $R_2$ is selected from the group consisting of H, F, Cl, and Br; with the proviso that at least one of $R_1$ and $R_2$ is selected from the group consisting of F, Cl, and Br.

3. The compound of claim 1, wherein the compound is of Formula (II), or a pharmaceutically acceptable salt thereof:

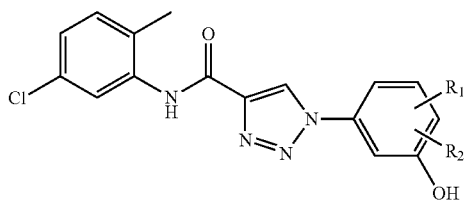

(II)

wherein $R_1$ is selected from the group consisting of H, halogen, and $C_1$-$C_3$ alkyl;

and $R_2$ is selected from the group consisting of H, $CF_3$, and halogen;

with the proviso that at least one of $R_1$ and $R_2$ is halogen or $CF_3$.

4. The compound of claim 1 selected from the group consisting of:

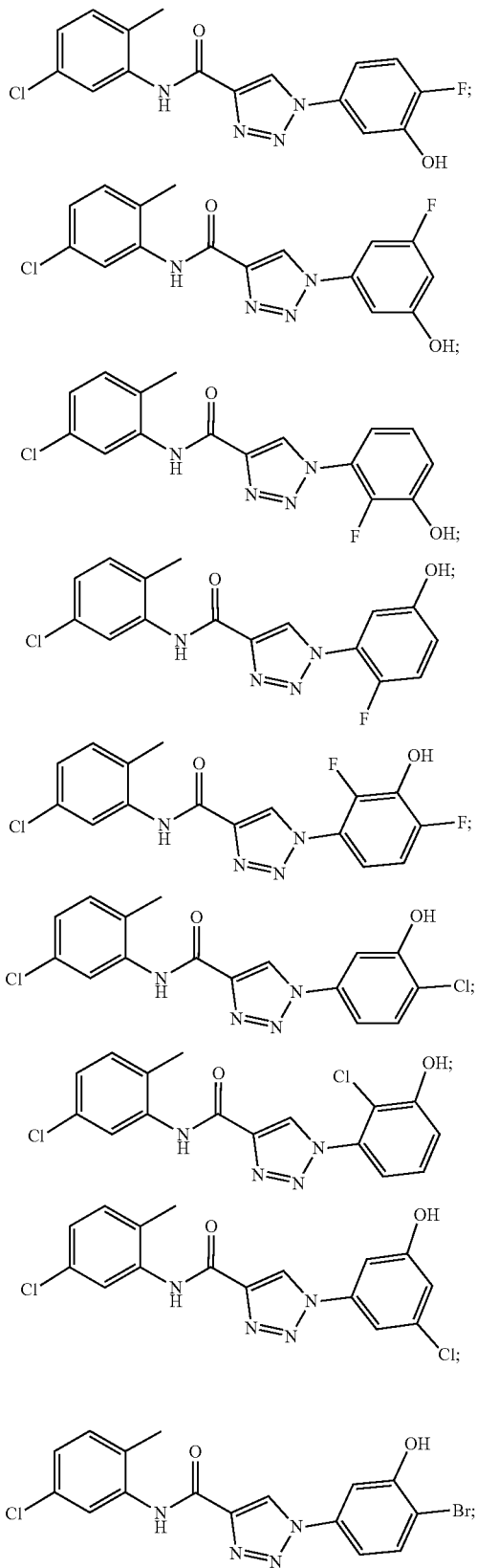

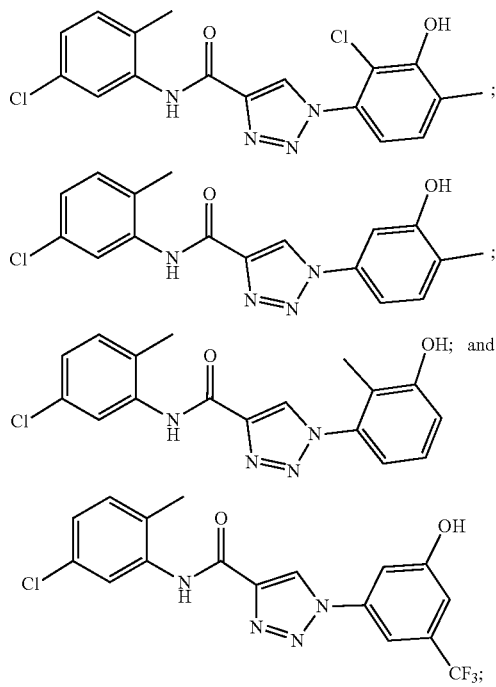

or a pharmaceutically acceptable salt thereof.

5. A pharmaceutical composition comprising a pharmaceutically effective amount of a compound of Formula (I), or a pharmaceutically acceptable salt thereof:

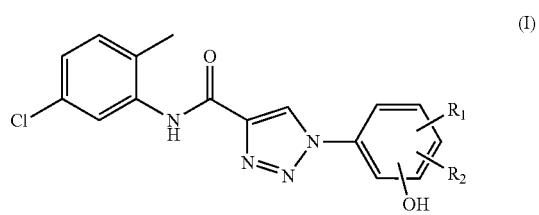

(I)

wherein $R_1$ is selected from the group consisting of H, halogen, and $C_1$-$C_3$ alkyl;

and $R_2$ is selected from the group consisting of H, $CF_3$, and halogen;

with the proviso that at least one of $R_1$ and $R_2$ is halogen or $CF_3$; and a pharmaceutically acceptable carrier or excipient.

6. The pharmaceutical composition of claim 5, wherein the compound of Formula (I) is selected from the group consisting of:

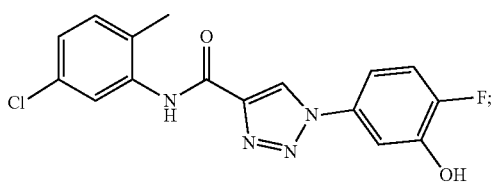

-continued

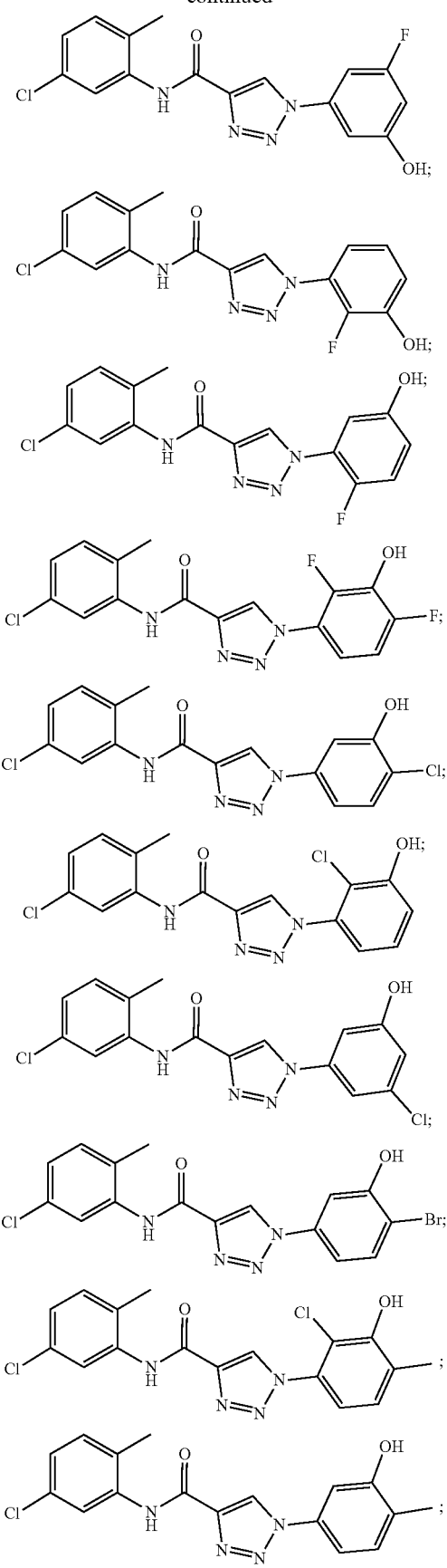

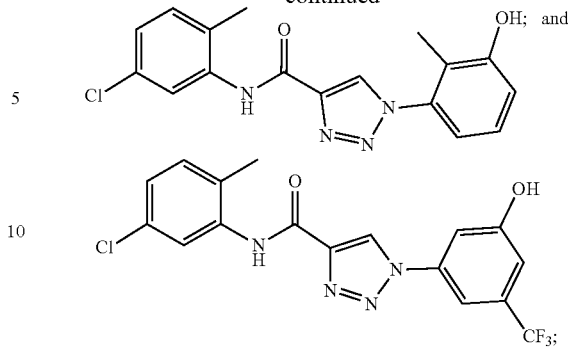

or a pharmaceutically acceptable salt thereof.

7. A method for treating in a human subject a disease selected from the group consisting of multiple sclerosis, amyotrophic lateral sclerosis, ischemic reperfusion injury, Alzheimer's disease, Huntington's disease, Parkinson's disease, insulin-induced hypoglycemia, cerebral ischemia, brain damage from epilepsy or experimental trauma, Bethlem myopathy, pancreatitis, hepatitis type A, hepatitis type B, hepatitis type C (type A, and/or B, and/or G), Type II diabetes, diabetic retinopathy, muscular dystrophy, traumatic brain injury, heart infarction, and stroke, the method comprising administering to the subject in need thereof a pharmaceutically effective amount of a compound of Formula (I), or a pharmaceutically acceptable salt thereof:

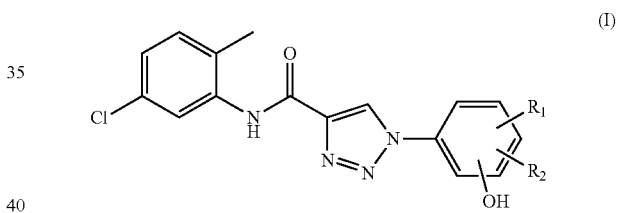

wherein $R_1$ is selected from the group consisting of H, halogen, and $C_1$-$C_3$ alkyl;

and $R_2$ is selected from the group consisting of H, $CF_3$, and halogen;

with the proviso that at least one of $R_1$ and $R_2$ is halogen or $CF_3$.

8. The method of claim 7, wherein the compound of Formula (I) is selected from the group consisting of:

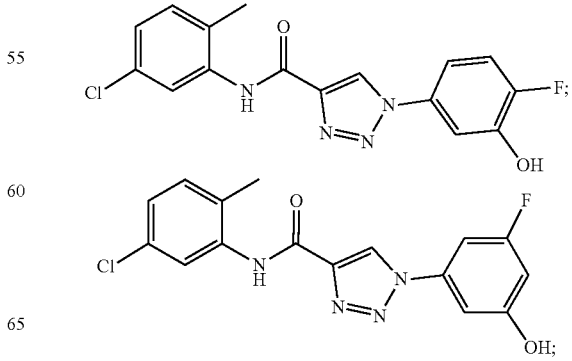

-continued
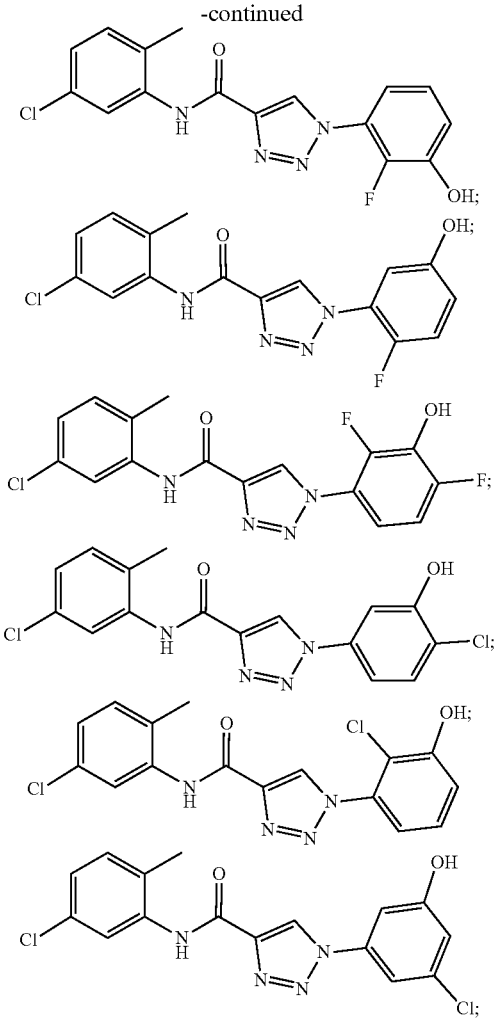
-continued
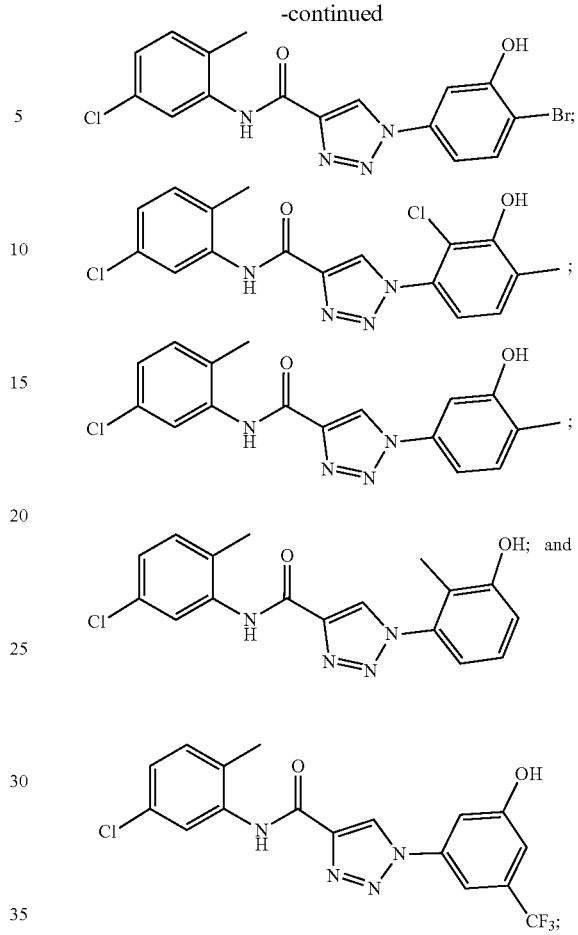
or a pharmaceutically acceptable salt thereof.
* * * * *